United States Patent
Cawse

(10) Patent No.: US 7,052,659 B1
(45) Date of Patent: May 30, 2006

(54) SEQUENTIAL HIGH THROUGHPUT SCREENING METHOD AND SYSTEM

(75) Inventor: James Norman Cawse, Pittsfield, MA (US)

(73) Assignee: General Electric Company, Schenectady, NY (US)

( * ) Notice: Subject to any disclaimer, the term of this patent is extended or adjusted under 35 U.S.C. 154(b) by 762 days.

(21) Appl. No.: 09/618,794

(22) Filed: Jul. 18, 2000

(51) Int. Cl.
*B01J 8/18* (2006.01)
*G05D 16/00* (2006.01)

(52) U.S. Cl. .................. 422/233; 422/63; 422/68.1; 422/81; 422/107; 422/112

(58) Field of Classification Search .......... 422/233, 422/232, 50, 63, 68.1, 81, 107, 112, 116
See application file for complete search history.

(56) References Cited

U.S. PATENT DOCUMENTS

| | | | |
|---|---|---|---|
| 3,784,826 A | * 1/1974 | Bagshawe et al. | .......... 250/106 |
| 5,020,237 A | * 6/1991 | Gross et al. | .......... 34/1 |
| 5,143,854 A | 9/1992 | Pirrung et al. | |
| 5,324,483 A | * 6/1994 | Cody et al. | .......... 422/131 |
| 5,366,555 A | 11/1994 | Kelly | |
| 5,563,095 A | * 10/1996 | Frey | .......... 437/141 |
| 5,688,696 A | 11/1997 | Lebl | |
| 5,880,972 A | 3/1999 | Horlbeck | |
| 5,976,813 A | 11/1999 | Beutel et al. | |
| 5,980,839 A | 11/1999 | Bier et al. | |
| 5,985,214 A | * 11/1999 | Styli et al. | .......... 422/65 |
| 5,959,297 A | 9/2000 | Weinberg et al. | |

OTHER PUBLICATIONS

Wolf et al., "An Evolutionary Approach in the Combinatorial Selection and Optimization of Catalytic Materials", Applied Catalysis A: General 200, 63–77 (2000).
Box, CG. E. P.; Hunter, W. G.; Hunter, J. S., Statistics for Experimenters; John Wiley:pp. 87–89, 228–231, New York 1978.

* cited by examiner

*Primary Examiner*—Andrew Wang
*Assistant Examiner*—My Chau T Tran
(74) *Attorney, Agent, or Firm*—Philip D. Freedman; Patrick K. Patnode

(57) ABSTRACT

A method and system for high-throughput screening of multiphase reactions are provided. In an exemplary embodiment the method includes the steps of sequentially loading a plurality of discrete combinations of reactants into a longitudinal reaction zone; reacting each of the combinations as it passes through the reaction zone to provide a continuously or an incrementally varying reaction product; and sequentially discharging the reaction product of each of combination from the reaction zone as reaction of each combination is completed.

6 Claims, 5 Drawing Sheets

FIG.4

| Step | Valve and Actuator Numbers | | | | | | | | Action |
|---|---|---|---|---|---|---|---|---|---|
| | 46 | 48 | 68 | 70 | 72 | 54 | 56 | 38 | |
| 1 | Open | Closed | Closed | Closed | Vented | Closed | Open | Off | Start System |
| 2 | Open | Closed | Closed | Open | Vented | Closed | Open | Off | Pressure Chamber |
| 3 | Open | Closed | Closed | Open | Vented | Closed | Open | Off | Vial to Lock |
| 4 | Closed | Closed | Closed | Open | Vented | Closed | Open | Off | Start Charge Lock |
| 5 | Closed | Closed | Open | Open | Vented | Closed | Open | Off | Pressure Lock |
| 6 | Closed | Open | Open | Open | Vented | Closed | Open | Off | Vial to Chamber |
| 7 | Closed | Closed | Closed | Open | Vented | Closed | Open | Off | Depressurize |
| 8 | Open | Closed | Closed | Open | Vented | Closed | Open | Off | End Charge Lock |
| 9 | Open | Closed | Closed | Open | Vented | Closed | Open | Off | Start Discharge Lock |
| 10 | Open | Closed | Closed | Open | Vented | Closed | Closed | Off | Pressure Lock |
| 11 | Open | Closed | Closed | Open | Gas | Closed | Closed | Off | Actuate Vial Shim |
| 12 | Open | Closed | Closed | Open | Gas | Closed | Closed | On | Drop Vial |
| 13 | Open | Closed | Closed | Open | Gas | Open | Closed | On | Release Next Vial |
| 14 | Open | Closed | Closed | Open | Gas | Closed | Closed | Off | Depressurize |
| 15 | Open | Closed | Closed | Open | Vented | Closed | Closed | Off | Depressurize |
| 16 | Open | Closed | Closed | Open | Vented | Closed | Open | Off | Discharge Vial |

SEQUENTIAL HIGH THROUGHPUT SCREENING METHOD AND SYSTEM

BACKGROUND

1. Field of the Invention

The present invention relates to a sequential high throughput screening (HTS) method and system.

2. Discussion of Related Art

In experimental reaction systems, each potential combination of reactant, catalyst and condition should be evaluated in a manner that provides correlation to performance in a production scale reactor. Combinatorial organic synthesis (COS) is an HTS methodology that was developed for pharmaceuticals. COS uses systematic and repetitive synthesis to produce diverse molecular entities formed from sets of chemical "building blocks." As with traditional research, COS relies on experimental synthesis methodology. However instead of synthesizing a single compound, COS exploits automation and miniaturization to produce large libraries of compounds through successive stages, each of which produces a chemical modification of an existing molecule of a preceding stage. The procedure provides large libraries of diverse compounds that can be screened for various activities.

The techniques used to prepare such libraries involve a stepwise or sequential coupling of building blocks to form the compounds of interest. For example, Pirrung et al., U.S. Pat. No. 5,143,854 ostensibly discloses a technique for generating arrays of peptides and other molecules using, for example, light-directed, spatially-addressable synthesis techniques. Pirrung synthesized polypeptide arrays on a substrate by attaching photoremovable groups to the surface of the substrate, exposing selected regions of the substrate to light to activate those regions, attaching an amino acid monomer with a photoremovable group to the activated region, and repeating the steps of activation and attachment until polypeptides of the desired length and sequences are synthesized.

According to the teachings of Pirrung, each synthesis requires bringing the array to reaction conditions, which requires time. If multiple synthesis steps are utilized as is often the case, each synthesis step should be carefully controlled to achieve uniform reaction conditions and time. Uniform reaction conditions and time periods are difficult to achieve with batch processing of array plates. Further, it is difficult to define and control reaction time with batch processing, since each array plate must be individually "ramped" to target synthesis conditions and then "backed off" from the conditions upon completing the reaction. Considerable manual manipulation may be required at startup and shutdown in adjusting controls, loading samples and bolting enclosures.

Additionally, a high pressure reactor large enough to hold an array plate would require thick walls that cause a delay in controlling temperature. Adjustment of temperature within the reactor always lags behind adjustment at the temperature control. This can be a serious problem where precise temperature control is required. For example, catalyst reaction studies typically require temperature measurement and control to better than ±2° C. (preferably ±0.5° C.).

There is a need for an HTS method and system to easily conduct multiple syntheses under identical or precisely controlled variable conditions and reaction times.

SUMMARY OF THE INVENTION

Accordingly, the present invention is directed to a method and apparatus for rapid screening of multiphase reactant systems. In one exemplary embodiment, the method includes the steps of sequentially loading a plurality of discrete combinations of reactants into a longitudinal reaction zone; reacting each of the combinations as it passes through the reaction zone to provide a continuously or an incrementally varying reaction product; and sequentially discharging the reaction product of each of combination from the reaction zone as reaction of each combination is completed.

In another aspect, the present invention is directed to a combinatorial chemical synthesis system, comprising a vessel having a charge port adapted to sequentially receive a plurality of discrete combinations of reactants and a reaction chamber in communication with the charge port and adapted to receive and enclose the plurality of reactant combinations disposed linearly within the chamber. A discharge port is placed in communication with the reaction chamber to sequentially discharge reaction products from the reaction chamber.

BRIEF DESCRIPTION OF THE DRAWINGS

Various features, aspects, and advantages of the present invention will become more apparent with reference to the following description, appended claims, and accompanying drawings, wherein

FIG. 4 is a table of sequences for carrying out an aspect of an embodiment of the present invention; and.

DETAILED DESCRIPTION OF PREFERRED EMBODIMENTS

Various embodiments of the present system are capable of fully unattended around the clock operation. Temperature, pressure, reaction time and reactant mix within a vessel reaction chamber can be fully automated to allow complete experimentation within precisely scheduled parameters. Sequential high throughput screening (HTS) methods can be conducted within the tubular reactor. For example, sequentially loaded combinations of reactants can be subjected to a varying parameter of reaction within a reaction zone of the reactor to provide continuously or incrementally varying product. The composition of each sequentially loaded combination can be controlled along with control of varying parameters of reaction within the reaction zone and sequentially produced products can be detected by a convention detecting means. The detected products can be correlated with the varying parameters of the reaction to provide a nonrandom combinatorial library of product.

These and other features will become apparent from the drawings and following detailed discussion, which by way of example without limitation describes preferred embodiments of the present invention.

Figure 1:
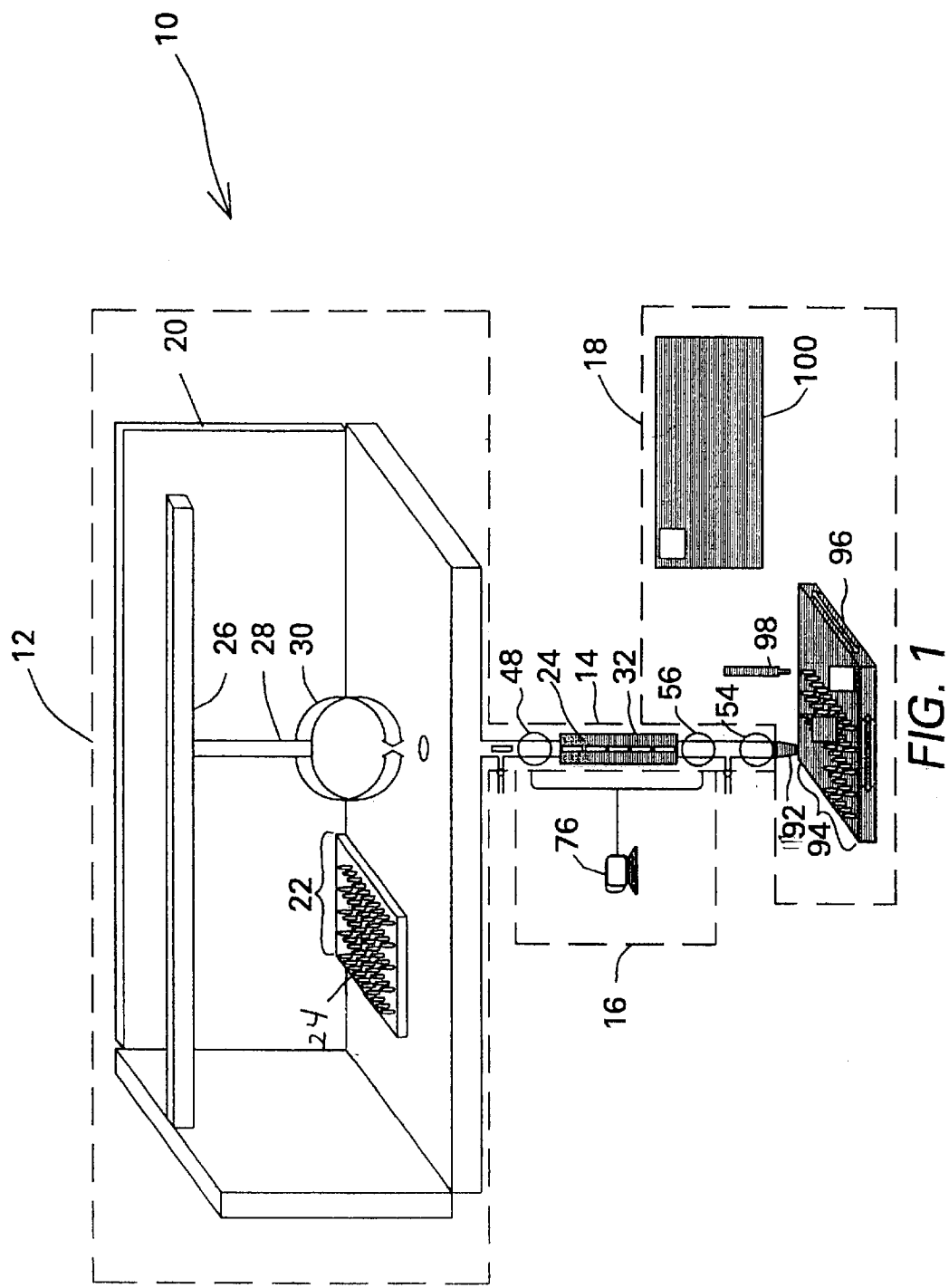
FIG. 1 is a schematic representation of an aspect of an embodiment of the present invention.

FIG. 1 is a schematic representation of an exemplary system 10 for sequential combinatorial chemical synthesis. FIG. 1 shows a system 10 including a sequential loader 12, a reaction vessel 14, a controller 16 and a detector 18. Loader 12 is shown having an encasement 20 enclosing an array 22 of vials 24 and a robotic frame 26 that includes an X-Y positioning arm 28 and an extendable vial manipulator 30.

Figure 2:
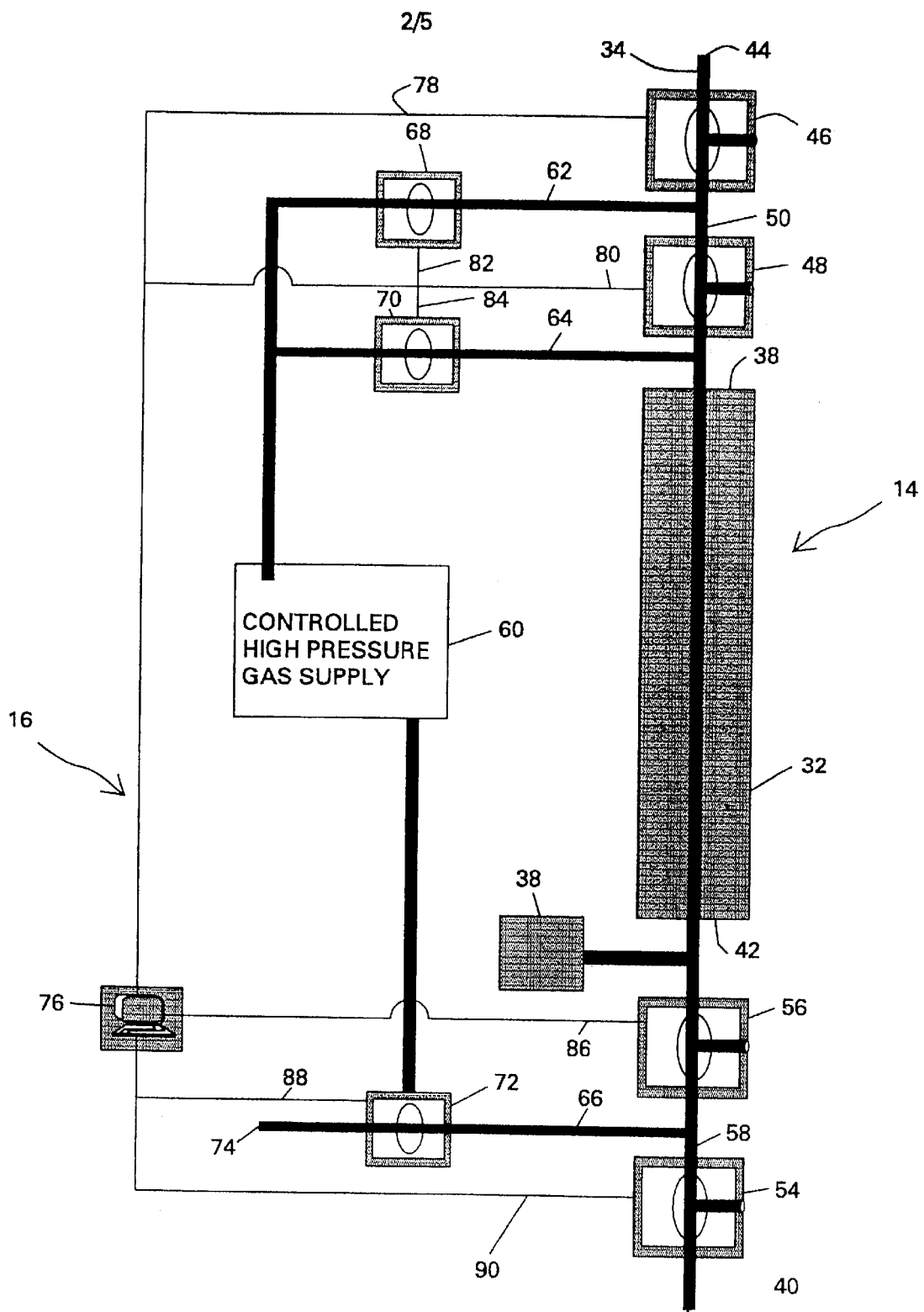
FIG. 2 is a schematic representation of an aspect of an embodiment of the present invention.

Reaction vessel 14 and controller 16 are shown in more detail in FIG. 2. Referring to both FIG. 1 and FIG. 2, vessel 14 includes a longitudinal reaction chamber 32 having a charge pipe 34 at a chamber first end 36 and a mechanical exit actuator 38 and a discharge pipe 40 at a chamber second end 42. Charge pipe 34 includes a charge port 44 for receiving sequentially loaded vials 24 from loader 12. Charge pipe 34 provides a conveyance for receiving vials 24 and conveying the vials in a sequential fashion to reaction chamber 32. Charge pipe 34 is provided with at least two valves—a charge actuator 46 and a charge gas lock actuator 48—that create a charge gas lock zone 50. Similarly, discharge pipe 40 includes a discharge port 52 for discharging vials 24 that have been sequentially transported through discharge pipe 40 from reaction chamber 32. In the embodiment shown, discharge pipe 40 is provided with at least two valves—a discharge gas lock actuator 54 and a discharge actuator 56 that create a discharge gas-lock zone 58.

Further shown in FIG. 2 is a gas supply and valving combination that illustrates a preferred feature. A gas pressure generator 60 supplies high pressure gas via a pipe 62 to charge pipe 34 and via a pipe 64 to charge gas lock zone 50. Also, gas pressure generator 60 supplies high pressure gas via a pipe 66 to discharge gas lock zone 58. Pipe 62 includes a charge lock pressure valve 68 that regulates pressure within charge gas lock zone 50. Pipe 64 includes a vessel valve 70 that regulates pressure within reaction vessel 14. Pipe 66 includes a three way discharge lock pressure valve 72 that regulates pressure within discharge gas lock zone 58 by injecting gas or by releasing pressure via a vent 74 to the atmosphere.

The system can include a controller as shown in FIG. 1 and FIG. 2. Controller 16 includes a processor 76, which can be a microprocessor, computer or the like. Processor 76 can be controllably connected to any or all of charge actuator 46, charge lock pressure valve 68, charge gas lock actuator 48, vessel valve 70, mechanical exit actuator 38, discharge gas lock actuator 54, vessel valve 70, and discharge actuator 56 via lines 78, 80, 82, 84, 86, 88, and 90 to provide a controlled sequential combinatorial chemical synthesis as hereinafter described.

Figure 3:
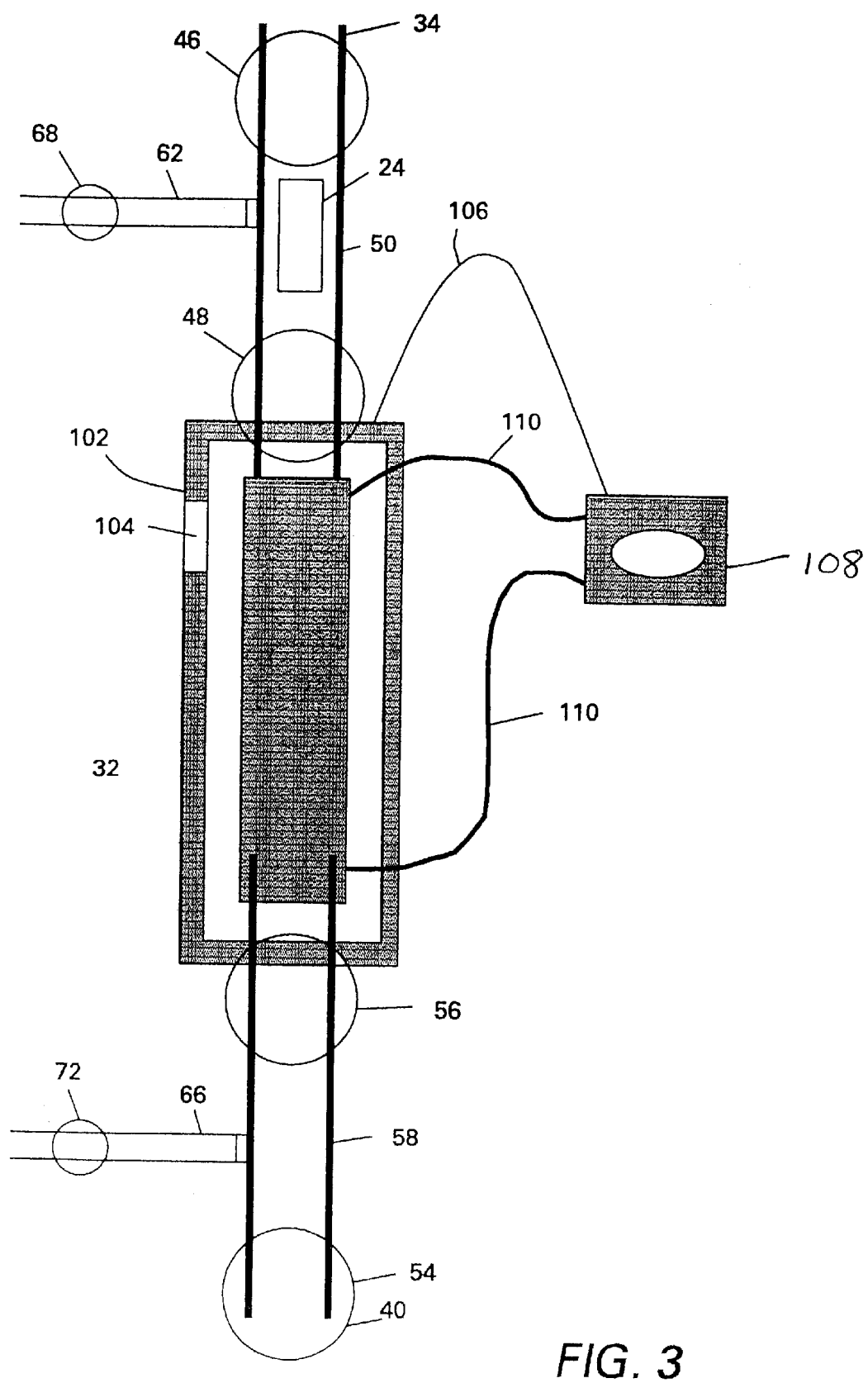
FIG. 3 is a schematic representation of an aspect of an embodiment of the present invention.

FIG. 1 shows a cut away side view of the reaction vessel 14 showing a stack of vials 24 progressing through longitudinal reaction chamber 32. FIG. 3 shows an electronic heating jacket 102 encompassing chamber 32. FIG. 3 further shows jacket 102 in combination with a structure for controlling temperature conditions within the chamber 32. The structure includes insulation 104 interposed within jacket 102, a high precision temperature measuring device 106, and a feedback heat controller 108. Examples of the high precision temperature measuring device include a thermocouple, thermistor, or platinum resistance thermometer. Heat controller 108 is attached to the interior of chamber 32 by leads 110. Electronic heating jacket 102 is shown with feedback control via temperature measuring device 106, which can be a probe, and heat controller 108. Other combinations can be used to control the temperature in chamber 32 such as a vapor heating jacket with pressure control, so long as the temperature can be controlled to within ±2° C., desirably within ±1° C. and preferably within ±0.5° C.

An HTS method can be conducted in the system shown in FIGS. 1, 2 and 3. In an exemplary embodiment of the method, an array of catalyst formulations is prepared according to any suitable procedure. For example, one procedure produces a homogeneous chemical reaction utilizing multiphase reactants. In this procedure, a formulation is prepared that represents a first reactant that is at least partially embodied in a liquid. During the subsequent reaction, the liquid of the first reactant can be contacted with a second reactant at least partially embodied in a gas. The liquid forms a film having a thickness sufficient to allow the reaction rate of the chemical reaction to be essentially independent of the mass transport rate of the second reactant into the liquid.

Each thin film formulation is deposited into a vial 24 to provide an array of reaction vials 24. Vial 24 is preferably formed of a rigid material that is chemically inert in the reaction environment. An example of an acceptable vial for many reactions is a glass vial. When dealing with liquids with low vapor pressures or with lengthy reactions, it may be desirable to provide a covering, such as a selectively permeable cap or a septum (not shown) incorporating a feed tube or needle disposed such that a gas is allowed to move freely into and out of vial 24 while depletion of liquid by evaporation is minimized. This arrangement allows an external pressure source to act upon the gas in the reactant environment while evaporation of liquid is limited. In most applications, suitable materials for the cap include polytetrafluoroethylene (PTFE) and expanded PTFE. A suitable cap for use with 2 ml glass vials is "Clear Snap Cap, PTFE/Silicone/PTFE with Starburst, 11 mm", part no. 27428, available from Supelco, Inc., Bellefonte, Pa.

The sequential loader 12 can be coordinated by controller 16 with a valving and actuator sequence described in the table of FIG. 4. With reference to FIG. 4, at commencement of operations, charge valve actuator 46 and discharge actuator 56 are open and the mechanical exit actuator 38 is deactivated (off); charge gas lock valve 46, charge lock pressure valve 68, vessel pressure valve 70 and discharge gas lock actuator 54 are closed and the three way gas lock valve 72 is in a vent position. The array of vials is positioned within sequential loader 12. Extendable X-Y positioning arm 28 grasps a vial 24 from the array 22 and positions the vial above charge port 44. Vessel pressure valve 70 is opened. A first vial from the array is charged by positioning arm 28 through open actuator 46 into charge gas lock zone 50 and the actuator is closed. Charge lock pressure valve 68 is opened and the charge lock zone 50 is pressurized to a pressure to match a reaction pressure within reaction chamber 32.

When pressure in charge lock zone 50 matches the reaction chamber pressure, charge lock pressure valve 68 is closed and charge gas lock actuator 48 is actuated to advance vial 24 into reaction chamber 32 and the actuator is closed. At this time, charge valve actuator 46 can be opened and charge gas lock zone 50 vented.

Vial contents are subjected to temperature and pressure reaction conditions within reaction chamber 32. Discharge actuator 56 is closed and three way discharge lock valve 72 is positioned to admit pressured gas from gas pressure generator 60 into discharge gas lock zone 58. Upon completion of reaction of the vial contents, mechanical exit actuator 38 is activated. Mechanical actuator 38 extends an arm immediately above vial 24 to prevent upper vials from dropping when a discharged vial drops from the chamber 32 into discharge gas lock zone 58. Discharge gas lock actuator 54 is then closed. Mechanical actuator 38 withdraws the arm, allowing vials above discharged vial 24 to drop so that the stack is now at the bottom of the tube.

Discharge gas lock zone 58 is depressurized by venting via three way valve 72 and discharge actuator 58 is opened to discharge vial 22 from zone 58 and thence from discharge pipe 40 to detector 18.

The above valve and actuator cycling procedure has been described with reference to processing of a single vial 22. However, a plurality of vials can be processed by repeating the FIG. 4 steps 2–8 a plurality of times to fill reaction chamber 32. Once chamber 32 is filled, then steps 2–16 are repeated to discharge a vial and to charge a vial to the reaction chamber.

Referring again to FIG. 1, the system also includes detector 18, which comprises a vial ejector 92 to direct a vial 24 from the reaction vessel discharge port 52 to a position within a vial array 94 that is retained on an X-Y positioning stage 96. The sequence of FIG. 4 can be coordinated with detector 18. Detector 18 further includes a fiber optic sensor 98 to sense the contents of the vials in combination with an analyzer 100. Analyzer 100 can utilize chromatography, infra red spectroscopy, mass spectroscopy, laser mass spectroscopy, microspectroscopy, NMR or the like to determine the constituency of each vial content.

In operation, X-Y positioning stage 96 of detector 18 positions an opening in array 94 directly beneath discharge port 52 so that when discharged, vial 24 falls cleanly into the array. Controller 16 registers the exact time a vial discharges from reactor vessel 14. X-Y positioning stage 96 moves array 94 beneath fiber optic sensor 98, which senses the contents of vial 24 for analysis by analyzer 100. For example, if the method and system of the invention is used to conduct a combinatorial synthesis to select a carbonylation catalyst and/or to determine optimum carbonylation reaction conditions, the analyzer analyzes the contents of the vial for carbonylated product. In this case, the analyzer can use Raman spectroscopy. The Raman peak is integrated using the analyzer electronics and the resulting data can be stored in the controller. Other analytical methods may be used as noted above.

The sequential combinatorial chemical synthesis herein described can be used with any suitable reactant system. For example, the system and method herein can be used for determining a method for producing diphenyl carbonate (DPC). Diphenyl carbonate (DPC) is useful, inter alia, as an intermediate in the preparation of polycarbonates. One method for producing DPC involves the carbonylation of a hydroxyaromatic compound (e.g., phenol) in the presence of a catalyst system. A carbonylation catalyst system typically includes a Group VIII B metal (e.g., palladium), a halide composition, and a combination of in organic co-catalysts (IOCCs). This one step reaction is typically carried out in a continuous reactor at high temperature and pressure with gas sparging. Insufficient gas/liquid mixing can result in low yields of DPC. Generally, testing of new catalyst systems has been accomplished at macro-scale and, because the mechanism of this carbonylation reaction is not fully understood, the identity of additional effective IOCCs has eluded practitioners. An embodiment of the present invention allows this homogeneous carbonylation reaction to be carried out in parallel with various potential catalyst systems and, consequently, this embodiment can be used to identify effective IOCCs for the carbonylation of phenol.

The following example is provided in order that those skilled in the art will be better able to understand and practice the present invention. This example is intended to serve as an illustration and not as a limitation of the present invention as defined in the claims herein

EXAMPLE

The economics of producing DPC by the above-mentioned carbonylation process is partially dependent on the number of moles of DPC produced per mole of Group VIII B metal utilized. In the following example, the Group VIII B metal utilized is palladium. For convenience, the number of moles of DPC produced per mole of palladium utilized is referred to as the palladium turnover number (Pd TON). Unless otherwise specified, all parts are by weight; all equivalents are relative to palladium; and all reactions are carried out in 2 ml glass vials at 90–100° C. in a 10% $O_2$ in CO atmosphere at an operating pressure of 95–110 atm. Reaction is generally 2–3 hours. Reaction products are verified by gas chromatography.

This example illustrates an identification of an active and selective catalyst for the production of aromatic carbonates. The procedure identifies the best catalyst from a complex chemical space, where the chemical space is defined as an assemblage of all possible experimental conditions defined by a set of variable parameters such as formulation ingredient identity or amount or process parameter such as reaction time, temperature, or pressure. In the Example, an initial iteration examines an experimental formulation consisting of six chemical species shown in TABLE 1 and the process parameters shown in TABLE 2.

TABLE 1

| | Formulation Type Parameter Variation | Formulation Amount Parameter Variation |
|---|---|---|
| Precious metal catalyst | Held Constant | Held Constant |
| Metal Catalyst 1 (M1) | Fe, Cu,Ni,Pb,Re (as their acetylacetonates) | 5, 20 (as molar ratios to precious metal catalyst) |
| Metal Catalyst 2 (M2) | V, W, Ce,La,Sn (as their acetylacetonates) | 5, 20 (as molar ratios to precious metal catalyst) |
| Cosolvent (CS) | Dimethylformamide (DMFA), Dimethylacetamide (DMAA), Tetrahydrofuran (THF), Diglyme (DiGly), Diethylacetamide (DEAA) | Varied independently in amount. Values are 500, 4000 (as molar ratios to precious metal catalyst) |
| Hydroxy-aromatic compound | Held constant | Sufficient added to achieve constant sample volume |

TABLE 2

| Process Parameter | Process Parameter Variation |
|---|---|
| Pressure | 1000 psi, 1500 psi (8% Oxygen in Carbon Monoxide) |
| Temperature | 100 C, 120 C |
| Reaction Time | 1 hour, 2 hours. |

The size of the initial chemical space defined by the parameters of TABLE 1 and TABLE 2 is calculated as 8000 possibilities. This is a very large experiment for conventional techniques. In Iteration 1 of the process, a 400-sample subset of the 8000 possibilities is selected to screen formulation factors (M1, M2, and CS) while maintaining full representation of the quantity and process factors. A Latin Square design strategy is applied to generate a 5×5 square of the formulation factors. A Latin Square is an orthogonal design that allows each value of each factor to combine with each value of each other factor exactly once. In the present instance, the Latin Square is represented in abbreviated form in TABLE 3 and fully expanded in TABLE 4.

TABLE 3

|  | M1 | | | | |
|---|---|---|---|---|---|
|  | Fe | Cu | Ni | Pb | Re |
| M2 V | DMFA | DMAA | THF | DiGly | DEAA |
| W | DMAA | THF | DiGly | DEAA | DMFA |
| Ce | THF | DiGly | DEAA | DMFA | DMAA |
| La | DiGly | DEAA | DMFA | DMAA | THF |
| Sn | DEAA | DMFA | DMAA | THF | DiGly |

TABLE 4

| M11 | M12 | Cosolvent | TON |
|---|---|---|---|
| Cu | V | DMFA | 2158 |
| Cu | W | DMAA | 2873 |
| Cu | Ce | THF | 1519 |
| Cu | La | DiGly | 1416 |
| Cu | Sn | DEAA | 1336 |
| Fe | V | DMAA | 3695 |
| Fe | W | THF | 4012 |
| Fe | Ce | DiGly | 2983 |
| Fe | La | DEAA | 2882 |
| Fe | Sn | DMFA | 3034 |
| Ni | V | THF | 347 |
| Ni | W | DiGly | 1122 |
| Ni | Ce | DEAA | 154 |
| Ni | La | DMFA | 44 |
| Ni | Sn | DMAA | 252 |
| Pb | V | DiGly | 522 |
| Pb | W | DEAA | 1127 |
| Pb | Ce | DMFA | 102 |
| Pb | La | DMAA | 139 |
| Pb | Sn | THF | 49 |
| Re | V | DEAA | 492 |
| Re | W | DMFA | 1184 |
| Re | Ce | DMAA | 298 |
| Re | La | THF | 89 |
| Re | Sn | DiGly | 55 |

A 16-run 2-level fractional factorial design is generated in the six process variables. A 2-level fractional factorial design is an experiment with >1 adjustable control parameters (factors), each of which takes on 2 values (levels). All possible combinations of the factors and levels are generated. A fraction of the possible combinations is selected to maximize the value of information gained from the experiment. In this Example, six process variables generate 64 possibilities, of which one-fourth is selected according to the fractional factorial design. TABLE 5 shows the selected possibilities.

TABLE 5

| M1 amt | M2 amp | CS amt | Pressure | Temp | Time |
|---|---|---|---|---|---|
| 5.00 | 20.00 | 500.00 | 1000.00 | 120.00 | 2.00 |
| 20.00 | 5.00 | 500.00 | 1200.00 | 120.00 | 2.00 |
| 5.00 | 5.00 | 500.00 | 1000.00 | 100.00 | 1.00 |
| 5.00 | 5.00 | 500.00 | 1200.00 | 100.00 | 2.00 |
| 5.00 | 5.00 | 4000.00 | 1000.00 | 120.00 | 2.00 |
| 5.00 | 20.00 | 500.00 | 1200.00 | 120.00 | 1.00 |
| 5.00 | 20.00 | 4000.00 | 1200.00 | 100.00 | 2.00 |
| 5.00 | 5.00 | 4000.00 | 1200.00 | 120.00 | 1.00 |
| 20.00 | 20.00 | 500.00 | 1200.00 | 100.00 | 1.00 |
| 20.00 | 20.00 | 4000.00 | 1200.00 | 120.00 | 2.00 |
| 20.00 | 5.00 | 4000.00 | 1000.00 | 100.00 | 2.00 |
| 20.00 | 20.00 | 500.00 | 1000.00 | 100.00 | 2.00 |
| 5.00 | 20.00 | 4000.00 | 1000.00 | 100.00 | 1.00 |
| 20.00 | 5.00 | 4000.00 | 1200.00 | 100.00 | 1.00 |
| 20.00 | 20.00 | 4000.00 | 1000.00 | 120.00 | 1.00 |
| 20.00 | 5.00 | 500.00 | 1000.00 | 120.00 | 1.00 |

A composite design is then generated in which each run of the fractional factorial design is performed at each combination of the Latin Square, for a total of 25×16=400 samples. The composite design is sorted by pressure, temperature and as shown in TABLE 6.

TABLE 6

| Sample | M1 | M2 | CS | M1 amt | M2 amt | CS amt | Pressure | Temp | Time |
|---|---|---|---|---|---|---|---|---|---|
| 1 | Cu | V | DMFA | 5 | 5 | 500 | 1000 | 100 | 1 |
| 2 | Cu | V | DMFA | 5 | 20 | 4000 | 1000 | 100 | 1 |
| 3 | Cu | W | DMAA | 5 | 5 | 500 | 1000 | 100 | 1 |
| 4 | Cu | W | DMAA | 5 | 20 | 4000 | 1000 | 100 | 1 |
| 5 | Cu | Ce | THF | 5 | 5 | 500 | 1000 | 100 | 1 |
| 6 | Cu | Ce | THF | 5 | 20 | 4000 | 1000 | 100 | 1 |
| 7 | Cu | La | DiGly | 5 | 5 | 500 | 1000 | 100 | 1 |
| 8 | Cu | La | DiGly | 5 | 20 | 4000 | 1000 | 100 | 1 |
| 9 | Cu | Sn | DEAA | 5 | 5 | 500 | 1000 | 100 | 1 |
| 10 | Cu | Sn | DEAA | 5 | 20 | 4000 | 1000 | 100 | 1 |
| 11 | Fe | V | DMAA | 5 | 5 | 500 | 1000 | 100 | 1 |
| 12 | Fe | V | DMAA | 5 | 20 | 4000 | 1000 | 100 | 1 |
| 13 | Fe | W | THF | 5 | 5 | 500 | 1000 | 100 | 1 |
| 14 | Fe | W | THF | 5 | 20 | 4000 | 1000 | 100 | 1 |
| 15 | Fe | Ce | DiGly | 5 | 5 | 500 | 1000 | 100 | 1 |
| 16 | Fe | Ce | DiGly | 5 | 20 | 4000 | 1000 | 100 | 1 |
| 17 | Fe | La | DEAA | 5 | 5 | 500 | 1000 | 100 | 1 |
| 18 | Fe | La | DEAA | 5 | 20 | 4000 | 1000 | 100 | 1 |
| 19 | Fe | Sn | DMFA | 5 | 5 | 500 | 1000 | 100 | 1 |
| 20 | Fe | Sn | DMFA | 5 | 20 | 4000 | 1000 | 100 | 1 |
| 21 | Ni | V | THF | 5 | 5 | 500 | 1000 | 100 | 1 |
| 22 | Ni | V | THF | 5 | 20 | 4000 | 1000 | 100 | 1 |
| 23 | Ni | W | DiGly | 5 | 5 | 500 | 1000 | 100 | 1 |
| 24 | Ni | W | DiGly | 5 | 20 | 4000 | 1000 | 100 | 1 |
| 25 | Ni | Ce | DEAA | 5 | 5 | 500 | 1000 | 100 | 1 |
| 26 | Ni | Ce | DEAA | 5 | 20 | 4000 | 1000 | 100 | 1 |
| 27 | Ni | La | DMFA | 5 | 5 | 500 | 1000 | 100 | 1 |
| 28 | Ni | La | DMFA | 5 | 20 | 4000 | 1000 | 100 | 1 |
| 29 | Ni | Sn | DMAA | 5 | 5 | 500 | 1000 | 100 | 1 |
| 30 | Ni | Sn | DMAA | 5 | 20 | 4000 | 1000 | 100 | 1 |

TABLE 6-continued

| Sample | M1 | M2 | CS | M1 amt | M2 amt | CS amt | Pressure | Temp | Time |
|---|---|---|---|---|---|---|---|---|---|
| 31 | Pb | V | DiGly | 5 | 5 | 500 | 1000 | 100 | 1 |
| 32 | Pb | V | DiGly | 5 | 20 | 4000 | 1000 | 100 | 1 |
| 33 | Pb | W | DEAA | 5 | 5 | 500 | 1000 | 100 | 1 |
| 34 | Pb | W | DEAA | 5 | 20 | 4000 | 1000 | 100 | 1 |
| 35 | Pb | Ce | DMFA | 5 | 5 | 500 | 1000 | 100 | 1 |
| 36 | Pb | Ce | DMFA | 5 | 20 | 4000 | 1000 | 100 | 1 |
| 37 | Pb | La | DMAA | 5 | 5 | 500 | 1000 | 100 | 1 |
| 38 | Pb | La | DMAA | 5 | 20 | 4000 | 1000 | 100 | 1 |
| 39 | Pb | Sn | THF | 5 | 5 | 500 | 1000 | 100 | 1 |
| 40 | Pb | Sn | THF | 5 | 20 | 4000 | 1000 | 100 | 1 |
| 41 | Re | V | DEAA | 5 | 5 | 500 | 1000 | 100 | 1 |
| 42 | Re | V | DEAA | 5 | 20 | 4000 | 1000 | 100 | 1 |
| 43 | Re | W | DMFA | 5 | 5 | 500 | 1000 | 100 | 1 |
| 44 | Re | W | DMFA | 5 | 20 | 4000 | 1000 | 100 | 1 |
| 45 | Re | Ce | DMAA | 5 | 5 | 500 | 1000 | 100 | 1 |
| 46 | Re | Ce | DMAA | 5 | 20 | 4000 | 1000 | 100 | 1 |
| 47 | Re | La | THF | 5 | 5 | 500 | 1000 | 100 | 1 |
| 48 | Re | La | THF | 5 | 20 | 4000 | 1000 | 100 | 1 |
| 49 | Re | Sn | DiGly | 5 | 5 | 500 | 1000 | 100 | 1 |
| 50 | Re | Sn | DiGly | 5 | 20 | 4000 | 1000 | 100 | 1 |
| 51 | Cu | V | DMFA | 20 | 5 | 4000 | 1000 | 100 | 2 |
| 52 | Cu | V | DMFA | 20 | 20 | 500 | 1000 | 100 | 2 |
| 53 | Cu | W | DMAA | 20 | 5 | 4000 | 1000 | 100 | 2 |
| 54 | Cu | W | DMAA | 20 | 20 | 500 | 1000 | 100 | 2 |
| 55 | Cu | Ce | THF | 20 | 5 | 4000 | 1000 | 100 | 2 |
| 56 | Cu | Ce | THF | 20 | 20 | 500 | 1000 | 100 | 2 |
| 57 | Cu | La | DiGly | 20 | 5 | 4000 | 1000 | 100 | 2 |
| 58 | Cu | La | DiGly | 20 | 20 | 500 | 1000 | 100 | 2 |
| 59 | Cu | Sn | DEAA | 20 | 5 | 4000 | 1000 | 100 | 2 |
| 60 | Cu | Sn | DEAA | 20 | 20 | 500 | 1000 | 100 | 2 |
| 61 | Fe | V | DMAA | 20 | 5 | 4000 | 1000 | 100 | 2 |
| 62 | Fe | V | DMAA | 20 | 20 | 500 | 1000 | 100 | 2 |
| 63 | Fe | W | THF | 20 | 5 | 4000 | 1000 | 100 | 2 |
| 64 | Fe | W | THF | 20 | 20 | 500 | 1000 | 100 | 2 |
| 65 | Fe | Ce | DiGly | 20 | 5 | 4000 | 1000 | 100 | 2 |
| 66 | Fe | Ce | DiGly | 20 | 20 | 500 | 1000 | 100 | 2 |
| 67 | Fe | La | DEAA | 20 | 5 | 4000 | 1000 | 100 | 2 |
| 68 | Fe | La | DEAA | 20 | 20 | 500 | 1000 | 100 | 2 |
| 69 | Fe | Sn | DMFA | 20 | 5 | 4000 | 1000 | 100 | 2 |
| 70 | Fe | Sn | DMFA | 20 | 20 | 500 | 1000 | 100 | 2 |
| 71 | Ni | V | THF | 20 | 5 | 4000 | 1000 | 100 | 2 |
| 72 | Ni | V | THF | 20 | 20 | 500 | 1000 | 100 | 2 |
| 73 | Ni | W | DiGly | 20 | 5 | 4000 | 1000 | 100 | 2 |
| 74 | Ni | W | DiGly | 20 | 20 | 500 | 1000 | 100 | 2 |
| 75 | Ni | Ce | DEAA | 20 | 5 | 4000 | 1000 | 100 | 2 |
| 76 | Ni | Ce | DEAA | 20 | 20 | 500 | 1000 | 100 | 2 |
| 77 | Ni | La | DMFA | 20 | 5 | 4000 | 1000 | 100 | 2 |
| 78 | Ni | La | DMFA | 20 | 20 | 500 | 1000 | 100 | 2 |
| 79 | Ni | Sn | DMAA | 20 | 5 | 4000 | 1000 | 100 | 2 |
| 80 | Ni | Sn | DMAA | 20 | 20 | 500 | 1000 | 100 | 2 |
| 81 | Pb | V | DiGly | 20 | 5 | 4000 | 1000 | 100 | 2 |
| 82 | Pb | V | DiGly | 20 | 20 | 500 | 1000 | 100 | 2 |
| 83 | Pb | W | DEAA | 20 | 5 | 4000 | 1000 | 100 | 2 |
| 84 | Pb | W | DEAA | 20 | 20 | 500 | 1000 | 100 | 2 |
| 85 | Pb | Ce | DMFA | 20 | 5 | 4000 | 1000 | 100 | 2 |
| 86 | Pb | Ce | DMFA | 20 | 20 | 500 | 1000 | 100 | 2 |
| 87 | Pb | La | DMAA | 20 | 5 | 4000 | 1000 | 100 | 2 |
| 88 | Pb | La | DMAA | 20 | 20 | 500 | 1000 | 100 | 2 |
| 89 | Pb | Sn | THF | 20 | 5 | 4000 | 1000 | 100 | 2 |
| 90 | Pb | Sn | THF | 20 | 20 | 500 | 1000 | 100 | 2 |
| 91 | Re | V | DEAA | 20 | 5 | 4000 | 1000 | 100 | 2 |
| 92 | Re | V | DEAA | 20 | 20 | 500 | 1000 | 100 | 2 |
| 93 | Re | W | DMFA | 20 | 5 | 4000 | 1000 | 100 | 2 |
| 94 | Re | W | DMFA | 20 | 20 | 500 | 1000 | 100 | 2 |
| 95 | Re | Ce | DMAA | 20 | 5 | 4000 | 1000 | 100 | 2 |
| 96 | Re | Ce | DMAA | 20 | 20 | 500 | 1000 | 100 | 2 |
| 97 | Re | La | THF | 20 | 5 | 4000 | 1000 | 100 | 2 |
| 98 | Re | La | THF | 20 | 20 | 500 | 1000 | 100 | 2 |
| 99 | Re | Sn | DiGly | 20 | 5 | 4000 | 1000 | 100 | 2 |
| 100 | Re | Sn | DiGly | 20 | 20 | 500 | 1000 | 100 | 2 |
| 101 | Cu | V | DMFA | 20 | 20 | 4000 | 1000 | 120 | 1 |
| 102 | Cu | V | DMFA | 20 | 5 | 500 | 1000 | 120 | 1 |
| 103 | Cu | W | DMAA | 20 | 20 | 4000 | 1000 | 120 | 1 |
| 104 | Cu | W | DMAA | 20 | 5 | 500 | 1000 | 120 | 1 |
| 105 | Cu | Ce | THF | 20 | 20 | 4000 | 1000 | 120 | 1 |
| 106 | Cu | Ce | THF | 20 | 5 | 500 | 1000 | 120 | 1 |
| 107 | Cu | La | DiGly | 20 | 20 | 4000 | 1000 | 120 | 1 |

TABLE 6-continued

| Sample | M1 | M2 | CS | M1 amt | M2 amt | CS amt | Pressure | Temp | Time |
|---|---|---|---|---|---|---|---|---|---|
| 108 | Cu | La | DiGly | 20 | 5 | 500 | 1000 | 120 | 1 |
| 109 | Cu | Sn | DEAA | 20 | 20 | 4000 | 1000 | 120 | 1 |
| 110 | Cu | Sn | DEAA | 20 | 5 | 500 | 1000 | 120 | 1 |
| 111 | Fe | V | DMAA | 20 | 20 | 4000 | 1000 | 120 | 1 |
| 112 | Fe | V | DMAA | 20 | 5 | 500 | 1000 | 120 | 1 |
| 113 | Fe | W | THF | 20 | 20 | 4000 | 1000 | 120 | 1 |
| 114 | Fe | W | THF | 20 | 5 | 500 | 1000 | 120 | 1 |
| 115 | Fe | Ce | DiGly | 20 | 20 | 4000 | 1000 | 120 | 1 |
| 116 | Fe | Ce | DiGly | 20 | 5 | 500 | 1000 | 120 | 1 |
| 117 | Fe | La | DEAA | 20 | 20 | 4000 | 1000 | 120 | 1 |
| 118 | Fe | La | DEAA | 20 | 5 | 500 | 1000 | 120 | 1 |
| 119 | Fe | Sn | DMFA | 20 | 20 | 4000 | 1000 | 120 | 1 |
| 120 | Fe | Sn | DMFA | 20 | 5 | 500 | 1000 | 120 | 1 |
| 121 | Ni | V | THF | 20 | 20 | 4000 | 1000 | 120 | 1 |
| 122 | Ni | V | THF | 20 | 5 | 500 | 1000 | 120 | 1 |
| 123 | Ni | W | DiGly | 20 | 20 | 4000 | 1000 | 120 | 1 |
| 124 | Ni | W | DiGly | 20 | 5 | 500 | 1000 | 120 | 1 |
| 125 | Ni | Ce | DEAA | 20 | 20 | 4000 | 1000 | 120 | 1 |
| 126 | Ni | Ce | DEAA | 20 | 5 | 500 | 1000 | 120 | 1 |
| 127 | Ni | La | DMFA | 20 | 20 | 4000 | 1000 | 120 | 1 |
| 128 | Ni | La | DMFA | 20 | 5 | 500 | 1000 | 120 | 1 |
| 129 | Ni | Sn | DMAA | 20 | 20 | 4000 | 1000 | 120 | 1 |
| 130 | Ni | Sn | DMAA | 20 | 5 | 500 | 1000 | 120 | 1 |
| 131 | Pb | V | DiGly | 20 | 20 | 4000 | 1000 | 120 | 1 |
| 132 | Pb | V | DiGly | 20 | 5 | 500 | 1000 | 120 | i |
| 133 | Pb | W | DEAA | 20 | 20 | 4000 | 1000 | 120 | 1 |
| 134 | Pb | W | DEAA | 20 | 5 | 500 | 1000 | 120 | 1 |
| 135 | Pb | Ce | DMFA | 20 | 20 | 4000 | 1000 | 120 | 1 |
| 136 | Pb | Ce | DMFA | 20 | 5 | 500 | 1000 | 120 | 1 |
| 137 | Pb | La | DMAA | 20 | 20 | 4000 | 1000 | 120 | 1 |
| 138 | Pb | La | DMAA | .20 | 5 | 500 | 1000 | 120 | 1 |
| 139 | Pb | Sn | THF | 20 | 20 | 4000 | 1000 | 120 | 1 |
| 140 | Pb | Sn | THF | 20 | 5 | 500 | 1000 | 120 | 1 |
| 141 | Re | V | DEAA | 20 | 20 | 4000 | 1000 | 120 | 1 |
| 142 | Re | V | DEAA | 20 | 5 | 500 | 1000 | 120 | 1 |
| 143 | Re | W | DMFA | 20 | 20 | 4000 | 1000 | 120 | 1 |
| 144 | Re | W | DMFA | 20 | 5 | 500 | 1000 | 120 | 1 |
| 145 | Re | Ce | DMAA | 20 | 20 | 4000 | 1000 | 120 | 1 |
| 146 | Re | Ce | DMAA | 20 | 5 | 500 | 1000 | 120 | 1 |
| 147 | Re | La | THF | 20 | 20 | 4000 | 1000 | 120 | 1 |
| 148 | Re | La | THF | 20 | 5 | 500 | 1000 | 120 | 1 |
| 149 | Re | Sn | DiGly | 20 | 20 | 4000 | 1000 | 120 | 1 |
| 150 | Re | Sn | DiGly | 20 | 5 | 500 | 1000 | 120 | 1 |
| 151 | Cu | V | DMFA | 5 | 20 | 500 | 1000 | 120 | 2 |
| 152 | Cu | V | DMFA | 5 | 5 | 4000 | 1000 | 120 | 2 |
| 153 | Cu | W | DMAA | 5 | 20 | 500 | 1000 | 120 | 2 |
| 154 | Cu | W | DMAA | 5 | 5 | 4000 | 1000 | 120 | 2 |
| 155 | Cu | Ce | THF | 5 | 20 | 500 | 1000 | 120 | 2 |
| 156 | Cu | Ce | THF | 5 | 5 | 4000 | 1000 | 120 | 2 |
| 157 | Cu | La | DiGly | 5 | 20 | 500 | 1000 | 120 | 2 |
| 158 | Cu | La | DiGly | 5 | 5 | 4000 | 1000 | 120 | 2 |
| 159 | Cu | Sn | DEAA | 5 | 20 | 500 | 1000 | 120 | 2 |
| 160 | Cu | Sn | DEAA | 5 | 5 | 4000 | 1000 | 120 | 2 |
| 161 | Fe | V | DMAA | 5 | 20 | 500 | 1000 | 120 | 2 |
| 162 | Fe | V | DMAA | 5 | 5 | 4000 | 1000 | 120 | 2 |
| 163 | Fe | W | THF | 5 | 20 | 500 | 1000 | 120 | 2 |
| 164 | Fe | W | THF | 5 | 5 | 4000 | 1000 | 120 | 2 |
| 165 | Fe | Ce | DiGly | 5 | 20 | 500 | 1000 | 120 | 2 |
| 166 | Fe | Ce | DiGly | 5 | 5 | 4000 | 1000 | 120 | 2 |
| 167 | Fe | La | DEAA | 5 | 20 | 500 | 1000 | 120 | 2 |
| 168 | Fe | La | DEAA | 5 | 5 | 4000 | 1000 | 120 | 2 |
| 169 | Fe | Sn | DMFA | 5 | 20 | 500 | 1000 | 120 | 2 |
| 170 | Fe | Sn | DMFA | 5 | 5 | 4000 | 1000 | 120 | 2 |
| 171 | Ni | V | THF | 5 | 20 | 500 | 1000 | 120 | 2 |
| 172 | Ni | V | THF | 5 | 5 | 4000 | 1000 | 120 | 2 |
| 173 | Ni | W | DiGly | 5 | 20 | 500 | 1000 | 120 | 2 |
| 174 | Ni | W | DiGly | 5 | 5 | 4000 | 1000 | 120 | 2 |
| 175 | Ni | Ce | DEAA | 5 | 20 | 500 | 1000 | 120 | 2 |
| 176 | Ni | Ce | DEAA | 5 | 5 | 4000 | 1000 | 120 | 2 |
| 177 | Ni | La | DMFA | 5 | 20 | i000 | 120 | 2 | |
| 178 | Ni | La | DMFA | 5 | 5 | 4000 | 1000 | 120 | 2 |
| 179 | Ni | Sn | DMAA | 5 | 20 | 500 | 1000 | 120 | 2 |
| 180 | Ni | Sn | DMAA | 5 | 5 | 4000 | 1000 | 120 | 2 |
| 181 | Pb | V | DiGly | 5 | 20 | 500 | 1000 | 120 | 2 |
| 182 | Pb | V | DiGly | 5 | 5 | 4000 | 1000 | 120 | 2 |
| 183 | Pb | W | DEAA | 5 | 20 | 500 | 1000 | 120 | 2 |
| 184 | Pb | W | DEAA | 5 | 5 | 4000 | 1000 | 120 | 2 |

TABLE 6-continued

| Sample | M1 | M2 | CS | M1 amt | M2 amt | CS amt | Pressure | Temp | Time |
|---|---|---|---|---|---|---|---|---|---|
| 185 | Pb | Ce | DMFA | 5 | 20 | 500 | 1000 | 120 | 2 |
| 186 | Pb | Ce | DMFA | 5 | 5 | 4000 | 1000 | 120 | 2 |
| 187 | Pb | La | DMAA | 5 | 20 | 500 | 1000 | 120 | 2 |
| 188 | Pb | La | DMAA | 5 | 5 | 4000 | 1000 | 120 | 2 |
| 189 | Pb | Sn | THF | 5 | 20 | 500 | 1000 | 120 | 2 |
| 190 | Pb | Sn | THF | 5 | 5 | 4000 | 1000 | 120 | 2 |
| 191 | Re | V | DEAA | 5 | 20 | 500 | 1000 | 120 | 2 |
| 192 | Re | V | DEAA | 5 | 5 | 4000 | 1000 | 120 | 2 |
| 193 | Re | W | DMFA | 5 | 20 | 500 | 1000 | 120 | 2 |
| 194 | Re | W | DMFA | 5 | 5 | 4000 | 1000 | 120 | 2 |
| 195 | Re | Ce | DMAA | 5 | 20 | 500 | 1000 | 120 | 2 |
| 196 | Re | Ce | DMAA | 5 | 5 | 4000 | 1000 | 120 | 2 |
| 197 | Re | La | THF | 5 | 20 | 500 | 1000 | 120 | 2 |
| 198 | Re | La | THF | 5 | 5 | 4000 | 1000 | 120 | 2 |
| 199 | Re | Sn | DiGly | 5 | 20 | 500 | 1000 | 120 | 2 |
| 200 | Re | Sn | DiGly | 5 | 5 | 4000 | 1000 | 120 | 2 |
| 201 | Cu | V | DMFA | 20 | 20 | 500 | 1200 | 100 | 1 |
| 202 | Cu | V | DMFA | 20 | 5 | 4000 | 1200 | 100 | 1 |
| 203 | Cu | W | DMAA | 20 | 20 | 500 | 1200 | 100 | 1 |
| 204 | Cu | W | DMAA | 20 | 5 | 4000 | 1200 | 100 | 1 |
| 205 | Cu | Ce | THF | 20 | 20 | 500 | 1200 | 100 | 1 |
| 206 | Cu | Ce | THF | 20 | 5 | 4000 | 1200 | 100 | 1 |
| 207 | Cu | La | DiGly | 20 | 20 | 500 | 1200 | 100 | 1 |
| 208 | Cu | La | DiGly | 20 | 5 | 4000 | 1200 | 100 | 1 |
| 209 | Cu | Sn | DEAA | 20 | 20 | 500 | 1200 | 100 | 1 |
| 210 | Cu | Sn | DEAA | 20 | 5 | 4000 | 1200 | 100 | 1 |
| 211 | Fe | V | DMAA | 20 | 20 | 500 | 1200 | 100 | 1 |
| 212 | Fe | V | DMAA | 20 | 5 | 4000 | 1200 | 100 | 1 |
| 213 | Fe | W | THF | 20 | 20 | 500 | 1200 | 100 | 1 |
| 214 | Fe | W | THF | 20 | 5 | 4000 | 1200 | 100 | 1 |
| 215 | Fe | Ce | DiGly | 20 | 20 | 500 | 1200 | 100 | 1 |
| 216 | Fe | Ce | DiGly | 20 | 5 | 4000 | 1200 | 100 | 1 |
| 217 | Fe | La | DEAA | 20 | 20 | 500 | 1200 | 100 | 1 |
| 218 | Fe | La | DEAA | 20 | 5 | 4000 | 1200 | 100 | 1 |
| 219 | Fe | Sn | DMFA | 20 | 20 | 500 | 1200 | 100 | 1 |
| 220 | Fe | Sn | DMFA | 20 | 5 | 4000 | 1200 | 100 | 1 |
| 221 | Ni | V | THF | 20 | 20 | 500 | 1200 | 100 | 1 |
| 222 | Ni | V | THF | 20 | 5 | 4000 | 1200 | 100 | 1 |
| 223 | Ni | W | DiGly | 20 | 20 | 500 | 1200 | 100 | 1 |
| 224 | Ni | W | DiGly | 20 | 5 | 4000 | 1200 | 100 | 1 |
| 225 | Ni | Ce | DEAA | 20 | 20 | 500 | 1200 | 100 | 1 |
| 226 | Ni | Ce | DEAA | 20 | 5 | 4000 | 1200 | 100 | 1 |
| 227 | Ni | La | DMFA | 20 | 20 | 500 | 1200 | 100 | 1 |
| 228 | Ni | La | DMFA | 20 | 5 | 4000 | 1200 | 100 | 1 |
| 229 | Ni | Sn | DMAA | 20 | 20 | 500 | 1200 | 100 | 1 |
| 230 | Ni | Sn | DMAA | 20 | 5 | 4000 | 1200 | 100 | 1 |
| 231 | Pb | V | DiGly | 20 | 20 | 500 | 1200 | 100 | 1 |
| 232 | Pb | V | DiGly | 20 | 5 | 4000 | 1200 | 100 | 1 |
| 233 | Pb | W | DEAA | 20 | 20 | 500 | 1200 | 100 | 1 |
| 234 | Pb | W | DEAA | 20 | 5 | 4000 | 1200 | 100 | 1 |
| 235 | Pb | Ce | DMFA | 20 | 20 | 500 | 1200 | 100 | 1 |
| 236 | Pb | Ce | DMFA | 20 | 5 | 4000 | 1200 | 100 | 1 |
| 237 | Pb | La | DMAA | 20 | 20 | 500 | 1200 | 100 | 1 |
| 238 | Pb | La | DMAA | 20 | 5 | 4000 | 1200 | 100 | 1 |
| 239 | Pb | Sn | THF | 20 | 20 | 500 | 1200 | 100 | 1 |
| 240 | Pb | Sn | THF | 20 | 5 | 4000 | 1200 | 100 | 1 |
| 241 | Re | V | DEAA | 20 | 20 | 500 | 1200 | 100 | 1 |
| 242 | Re | V | DEAA | 20 | 5 | 4000 | 1200 | 100 | 1 |
| 243 | Re | W | DMFA | 20 | 20 | 500 | 1200 | 100 | 1 |
| 244 | Re | W | DMFA | 20 | 5 | 4000 | 1200 | 100 | 1 |
| 245 | Re | Ce | DMAA | 20 | 20 | 500 | 1200 | 100 | 1 |
| 246 | Re | Ce | DMAA | 20 | 5 | 4000 | 1200 | 100 | 1 |
| 247 | Re | La | THF | 20 | 20 | 500 | 1200 | 100 | 1 |
| 248 | Re | La | THF | 20 | 5 | 4000 | 1200 | 100 | 1 |
| 249 | Re | Sn | DiGly | 20 | 20 | 500 | 1200 | 100 | 1 |
| 250 | Re | Sn | DiGly | 20 | 5 | 4000 | 1200 | 100 | 1 |
| 251 | Cu | V | DMFA | 5 | 5 | 500 | 1200 | 100 | 2 |
| 252 | Cu | V | DMFA | 5 | 20 | 4000 | 1200 | 100 | 2 |
| 253 | Cu | W | DMAA | 5 | 5 | 500 | 1200 | 100 | 2 |
| 254 | Cu | W | DMAA | 5 | 20 | 4000 | 1200 | 100 | 2 |
| 255 | Cu | Ce | THF | 5 | 5 | 500 | 1200 | 100 | 2 |
| 256 | Cu | Ce | THF | 5 | 20 | 4000 | 1200 | 100 | 2 |
| 257 | Cu | La | DiGly | 5 | 5 | 500 | 1200 | 100 | 2 |
| 258 | Cu | La | DiGly | 5 | 20 | 4000 | 1200 | 100 | 2 |
| 259 | Cu | Sn | DEAA | 5 | 5 | 500 | 1200 | 100 | 2 |
| 260 | Cu | Sn | DEAA | 5 | 20 | 4000 | 1200 | 100 | 2 |
| 261 | Fe | V | DMAA | 5 | 5 | 500 | 1200 | 100 | 2 |

TABLE 6-continued

| Sample | M1 | M2 | CS | M1 amt | M2 amt | CS amt | Pressure | Temp | Time |
|---|---|---|---|---|---|---|---|---|---|
| 262 | Fe | V | DMAA | 5 | 20 | 4000 | 1200 | 100 | 2 |
| 263 | Fe | W | THF | 5 | 5 | 500 | 1200 | 100 | 2 |
| 264 | Fe | W | THF | 5 | 20 | 4000 | 1200 | 100 | 2 |
| 265 | Fe | Ce | DiGly | 5 | 5 | 500 | 1200 | 100 | 2 |
| 266 | Fe | Ce | DiGly | 5 | 20 | 4000 | 1200 | 100 | 2 |
| 267 | Fe | La | DEAA | 5 | 5 | 500 | 1200 | 100 | 2 |
| 268 | Fe | La | DEAA | 5 | 20 | 4000 | 1200 | 100 | 2 |
| 269 | Fe | Sn | DMFA | 5 | 5 | 500 | 1200 | 100 | 2 |
| 270 | Fe | Sn | DMFA | 5 | 20 | 4000 | 1200 | 100 | 2 |
| 271 | Ni | V | THF | 5 | 5 | 500 | 1200 | 100 | 2 |
| 272 | Ni | V | THF | 5 | 20 | 4000 | 1200 | 100 | 2 |
| 273 | Ni | W | DiGly | 5 | 5 | 500 | 1200 | 100 | 2 |
| 274 | Ni | W | DiGly | 5 | 20 | 4000 | 1200 | 100 | 2 |
| 275 | Ni | Ce | DEAA | 5 | 5 | 500 | 1200 | 100 | 2 |
| 276 | Ni | Ce | DEAA | 5 | 20 | 4000 | 1200 | 100 | 2 |
| 277 | Ni | La | DMFA | 5 | 5 | 500 | 1200 | 100 | 2 |
| 278 | Ni | La | DMFA | 5 | 20 | 4000 | 1200 | 100 | 2 |
| 279 | Ni | Sn | DMAA | 5 | 5 | 500 | 1200 | 100 | 2 |
| 280 | Ni | Sn | DMAA | 5 | 20 | 4000 | 1200 | 100 | 2 |
| 281 | Pb | V | DiGly | 5 | 5 | 500 | 1200 | 100 | 2 |
| 282 | Pb | V | DiGly | 5 | 20 | 4000 | 1200 | 100 | 2 |
| 283 | Pb | W | DEAA | 5 | 5 | 500 | 1200 | 100 | 2 |
| 284 | Pb | W | DEAA | 5 | 20 | 4000 | 1200 | 100 | 2 |
| 285 | Pb | Ce | DMFA | 5 | 5 | 500 | 1200 | 100 | 2 |
| 286 | Pb | Ce | DMFA | 5 | 20 | 4000 | 1200 | 100 | 2 |
| 287 | Pb | La | DMAA | 5 | 5 | 500 | 1200 | 100 | 2 |
| 288 | Pb | La | DMAA | 5 | 20 | 4000 | 1200 | 100 | 2 |
| 289 | Pb | Sn | THF | 5 | 5 | 500 | 1200 | 100 | 2 |
| 290 | Pb | Sn | THF | 5 | 20 | 4000 | 1200 | 100 | 2 |
| 291 | Re | V | DEAA | 5 | 5 | 500 | 1200 | 100 | 2 |
| 292 | Re | V | DEAA | 5 | 20 | 4000 | 1200 | 100 | 2 |
| 293 | Re | W | DMFA | 5 | 5 | 500 | 1200 | 100 | 2 |
| 294 | Re | W | DMFA | 5 | 20 | 4000 | 1200 | 100 | 2 |
| 295 | Re | Ce | DMAA | 5 | 5 | 500 | 1200 | 100 | 2 |
| 296 | Re | Ce | DMAA | 5 | 20 | 4000 | 1200 | 100 | 2 |
| 297 | Re | La | THF | 5 | 5 | 500 | 1200 | 100 | 2 |
| 298 | Re | La | THF | 5 | 20 | 4000 | 1200 | 100 | 2 |
| 299 | Re | Sn | DiGly | 5 | 5 | 500 | 1200 | 100 | 2 |
| 300 | Re | Sn | DiGly | 5 | 20 | 4000 | 1200 | 100 | 2 |
| 301 | Cu | V | DMFA | 5 | 20 | 500 | 1200 | 120 | 1 |
| 302 | Cu | V | DMFA | 5 | 5 | 4000 | 1200 | 120 | 1 |
| 303 | Cu | W | DMAA | 5 | 20 | 500 | 1200 | 120 | 1 |
| 304 | Cu | W | DMAA | 5 | 5 | 4000 | 1200 | 120 | 1 |
| 305 | Cu | Ce | THF | 5 | 20 | 500 | 1200 | 120 | 1 |
| 306 | Cu | Ce | THF | 5 | 5 | 4000 | 1200 | 120 | 1 |
| 307 | Cu | La | DiGly | 5 | 20 | 500 | 1200 | 120 | 1 |
| 308 | Cu | La | DiGly | 5 | 5 | 4000 | 1200 | 120 | 1 |
| 309 | Cu | Sn | DEAA | 5 | 20 | 500 | 1200 | 120 | 1 |
| 310 | Cu | Sn | DEAA | 5 | 5 | 4000 | 1200 | 120 | 1 |
| 311 | Fe | V | DMAA | 5 | 20 | 500 | 1200 | 120 | 1 |
| 312 | Fe | V | DMAA | 5 | 5 | 4000 | 1200 | 120 | 1 |
| 313 | Fe | W | THF | 5 | 20 | 500 | 1200 | 120 | 1 |
| 314 | Fe | W | THF | 5 | 5 | 4000 | 1200 | 120 | 1 |
| 315 | Fe | Ce | DiGly | 5 | 20 | 500 | 1200 | 120 | 1 |
| 316 | Fe | Ce | DiGly | 5 | 5 | 4000 | 1200 | 120 | 1 |
| 317 | Fe | La | DEAA | 5 | 20 | 500 | 1200 | 120 | 1 |
| 318 | Fe | La | DEAA | 5 | 5 | 4000 | 1200 | 120 | 1 |
| 319 | Fe | Sn | DMFA | 5 | 20 | 500 | 1200 | 120 | i |
| 320 | Fe | Sn | DMFA | 5 | 5 | 4000 | 1200 | 120 | 1 |
| 321 | Ni | V | THF | 5 | 20 | 500 | 1200 | 120 | 1 |
| 322 | Ni | V | THF | 5 | 5 | 4000 | 1200 | 120 | 1 |
| 323 | Ni | W | DiGly | 5 | 20 | 500 | 1200 | 120 | 1 |
| 324 | Ni | W | DiGly | 5 | 5 | 4000 | 1200 | 120 | 1 |
| 325 | Ni | Ce | DEAA | 5 | 20 | 500 | 1200 | 120 | 1 |
| 326 | Ni | Ce | DEAA | 5 | 5 | 4000 | 1200 | 120 | 1 |
| 327 | Ni | La | DMFA | 5 | 20 | 500 | 1200 | 120 | 1 |
| 328 | Ni | La | DMFA | 5 | 5 | 4000 | 1200 | 120 | 1 |
| 329 | Ni | Sn | DMAA | 5 | 20 | 500 | 1200 | 120 | 1 |
| 330 | Ni | Sn | DMAA | 5 | 5 | 4000 | 1200 | 120 | 1 |
| 331 | Pb | V | DiGly | 5 | 20 | 500 | 1200 | 120 | 1 |
| 332 | Pb | V | DiGly | 5 | 5 | 4000 | 1200 | 120 | 1 |
| 333 | Pb | W | DEAA | 5 | 20 | 500 | 1200 | 120 | 1 |
| 334 | Pb | W | DEAA | 5 | 5 | 4000 | 1200 | 120 | 1 |
| 335 | Pb | Ce | DMFA | 5 | 20 | 500 | 1200 | 120 | 1 |
| 336 | Pb | Ce | DMFA | 5 | 5 | 4000 | 1200 | 120 | 1 |
| 337 | Pb | La | DMAA | 5 | 20 | 500 | 1200 | 120 | 1 |
| 338 | Pb | La | DMAA | 5 | 5 | 4000 | 1200 | 120 | 1 |

TABLE 6-continued

| Sample | M1 | M2 | CS | M1 amt | M2 amt | CS amt | Pressure | Temp | Time |
|---|---|---|---|---|---|---|---|---|---|
| 339 | Pb | Sn | THF | 5 | 20 | 500 | 1200 | 120 | 1 |
| 340 | Pb | Sn | THF | 5 | 5 | 4000 | 1200 | 120 | 1 |
| 341 | Re | V | DEAA | 5 | 20 | 500 | 1200 | 120 | 1 |
| 342 | Re | V | DEAA | 5 | 5 | 4000 | 1200 | 120 | 1 |
| 343 | Re | W | DMFA | 5 | 20 | 500 | 1200 | 120 | 1 |
| 344 | Re | W | DMFA | 5 | 5 | 4000 | 1200 | 120 | 1 |
| 345 | Re | Ce | DMAA | 5 | 20 | 500 | 1200 | 120 | 1 |
| 346 | Re | Ce | DMAA | 5 | 5 | 4000 | 1200 | 120 | 1 |
| 347 | Re | La | THF | 5 | 20 | 5{}0 | 1200 | 120 | 1 |
| 348 | Re | La | THF | 5 | 5 | 4000 | 1200 | 120 | 1 |
| 349 | Re | Sn | DiGly | 5 | 20 | 500 | 1200 | 120 | 1 |
| 350 | Re | Sn | DiGly | 5 | 5 | 4000 | 1200 | 120 | 1 |
| 351 | Cu | V | DMFA | 20 | 5 | 500 | 1200 | 120 | 2 |
| 352 | Cu | V | DMFA | 20 | 20 | 4000 | 1200 | 120 | 2 |
| 353 | Cu | W | DMAA | 20 | 5 | 500 | 1200 | 120 | 2 |
| 354 | Cu | W | DMAA | 20 | 20 | 4000 | 1200 | 120 | 2 |
| 355 | Cu | Ce | THF | 20 | 5 | 500 | 1200 | 120 | 2 |
| 356 | Cu | Ce | THF | 20 | 20 | 4000 | 1200 | 120 | 2 |
| 357 | Cu | La | DiGly | 20 | 5 | 500 | 1200 | 120 | 2 |
| 358 | Cu | La | DiGly | 20 | 20 | 4000 | 1200 | 120 | 2 |
| 359 | Cu | Sn | DEAA | 20 | 5 | 500 | 1200 | 120 | 2 |
| 360 | Cu | Sn | DEAA | 20 | 20 | 4000 | 1200 | 120 | 2 |
| 361 | Fe | V | DMAA | 20 | 5 | 500 | 1200 | 120 | 2 |
| 362 | Fe | V | DMAA | 20 | 20 | 4000 | 1200 | 120 | 2 |
| 363 | Fe | W | THF | 20 | 5 | 500 | 1200 | 120 | 2 |
| 364 | Fe | W | THF | 20 | 20 | 4000 | 1200 | 120 | 2 |
| 365 | Fe | Ce | DiGly | 20 | 5 | 500 | 1200 | 120 | 2 |
| 366 | Fe | Ce | DiGly | 20 | 20 | 4000 | 1200 | 120 | 2 |
| 367 | Fe | La | DEAA | 20 | 5 | 500 | 1200 | 120 | 2 |
| 368 | Fe | La | DEAA | 20 | 20 | 4000 | 1200 | 120 | 2 |
| 369 | Fe | Sn | DMFA | 20 | 5 | 500 | 1200 | 120 | 2 |
| 370 | Fe | Sn | DMFA | 20 | 20 | 4000 | 1200 | 120 | 2 |
| 371 | Ni | V | THF | 20 | 5 | 500 | 1200 | 120 | 2 |
| 372 | Ni | V | THF | 20 | 20 | 4000 | 1200 | 120 | 2 |
| 373 | Ni | W | DiGly | 20 | 5 | 500 | 1200 | 120 | 2 |
| 374 | Ni | W | DiGly | 20 | 20 | 4000 | 1200 | 120 | 2 |
| 375 | Ni | Ce | DEAA | 20 | 5 | 500 | 1200 | 120 | 2 |
| 376 | Ni | Ce | DEAA | 20 | 20 | 4000 | 1200 | 120 | 2 |
| 377 | Ni | La | DMFA | 20 | 5 | 500 | 1200 | 120 | 2 |
| 378 | Ni | La | DMFA | 20 | 20 | 4000 | 1200 | 120 | 2 |
| 379 | Ni | Sn | DMAA | 20 | 5 | 500 | 1200 | 120 | 2 |
| 380 | Ni | Sn | DMAA | 20 | 20 | 4000 | 1200 | 120 | 2 |
| 381 | Pb | V | DiGly | 20 | 5 | 500 | 1200 | 120 | 2 |
| 382 | Pb | V | DiGly | 20 | 20 | 4000 | 1200 | 120 | 2 |
| 383 | Pb | W | DEAA | 20 | 5 | 500 | 1200 | 120 | 2 |
| 384 | Pb | W | DEAA | 20 | 20 | 4000 | 1200 | 120 | 2 |
| 385 | Pb | Ce | DMFA | 20 | 5 | 500 | 1200 | 120 | 2 |
| 386 | Pb | Ce | DMFA | 20 | 20 | 4000 | 1200 | 120 | 2 |
| 387 | Pb | La | DMAA | 20 | 5 | 500 | 1200 | 120 | 2 |
| 388 | Pb | La | DMAA | 20 | 20 | 4000 | 1200 | 120 | 2 |
| 389 | Pb | Sn | THF | 20 | 5 | 500 | 1200 | 120 | 2 |
| 390 | Pb | Sn | THF | 20 | 20 | 4000 | 1200 | 120 | 2 |
| 391 | Re | V | DEAA | 20 | 5 | 500 | 1200 | 120 | 2 |
| 392 | Re | V | DEAA | 20 | 20 | 4000 | 1200 | 120 | 2 |
| 393 | Re | W | DMFA | 20 | 5 | 500 | 1200 | 120 | 2 |
| 394 | Re | W | DMFA | 20 | 20 | 4000 | 1200 | 120 | 2 |
| 395 | Re | Ce | DMAA | 20 | 5 | 500 | 1200 | 120 | 2 |
| 396 | Re | Ce | DMAA | 20 | 20 | 4000 | 1200 | 120 | 2 |
| 397 | Re | La | THF | 20 | 5 | 500 | 1200 | 120 | 2 |
| 398 | Re | La | THF | 20 | 20 | 4000 | 1200 | 120 | 2 |
| 399 | Re | Sn | DiGly | 20 | 5 | 500 | 1200 | 120 | 2 |
| 400 | Re | Sn | DiGly | 20 | 20 | 4000 | 1200 | 120 | 2 |

In this evaluation, each of the metal acetylacetonates, the DMAA, and the DFMA is made up as a stock solution in phenol. An appropriate quantity of each stock solution is then combined using a Hamilton MicroLab 4000 laboratory robot into a single vial for mixing. For example, the stock solutions to produce vials 1, 65, 129, 193, 257, 321, 385, and 449, are 0.01 molar Pd(acetylacetonate), 0.01 molar each of Fe (acetylacetonate) and V(acetylacetonate) and 5 molar DMFA. Ten ml of each stock solution is produced by manual weighing and mixing. Aliquots of the stock solutions are measured as follows in TABLE 7. The mixture is stirred using a miniature magnetic stirrer, and then 25 microliters are measured out to each of eight 2-ml vials using the Hamilton robot. This small quantity forms a thin film on the vial bottom.

TABLE 7

| | |
|---|---|
| 0.01 molar Pd(acetylacetonate) | 25 microliters |
| 0.01 molar Fe(acetylacetonate) | 125 microliters |
| 0.01 molar V(acetylacetonate) | 125 microliters |

TABLE 7-continued

| | |
|---|---|
| 5 molar DMFA | 25 microliters |
| Pure Phenol | 700 microliters |

After each mixture is made, mixed, and distributed to 2-ml vials, the vials are cappeed using "star" caps (which allow gas exchange with the environment) and placed in the loader of FIG. 1. The tubular reactor system is heated and pressurized to the conditions shown as Block 1 in TABLE 8 and the automatic loading and processing procedure dicussed above is begun. Loading and unloading times are controlled so that each vial is in the heated reaction zone for the time shown in Block 1: 1 hour. The reaction zone can accommodate a stack of 20 vials. A new vial is added every three minutes until the stack is full, then one vial is removed and another added every three minutes thereafter. As vials progress down the stack, their exposure time is 20×3 minutes=60 minutes=1 hour.

TABLE 8

| Block | Pressure (psi) | Temperature (° C.) | Time (hours) |
|---|---|---|---|
| 1 | 1000 | 100 | 1 |
| 2 | 1000 | 100 | 2 |
| 3 | 1000 | 120 | 1 |
| 4 | 1000 | 120 | 2 |
| 5 | 1200 | 100 | 1 |
| 6 | 1200 | 100 | 2 |
| 7 | 1200 | 120 | 1 |
| 8 | 1200 | 120 | 2 |

As each vial exits the reactor, it falls into a new array and is analyzed by gas-liquid chromatography.

Performance is expressed numerically as a catalyst turn-over number or TON. TON is defined as the number of moles of aromatic carbonate produced per mole of Palladium catalyst charged.

When all rows with the same pressure, temperature and reaction time have been processed, the pressure and temperature are adjusted to new conditions. The timing is adjusted and a next row is processed. This iteration is repeated until all conditions have been run. The performance of each vial is given in the column "TON" of TABLE 4. The TON's of TABLE 4 are averaged by each formulation component to give the results shown in TABLE 9. TAB:LE 9 shows that average TON is significantly larger for M1=Fe or Cu; M2=V or W; and cosolvent=DMFA or DMAA. These are selected for a second iteration.

TABLE 9

| M1 | M1ave | M2 | M2ave | Cosolvent | CS ave |
|---|---|---|---|---|---|
| Cu | 1860.3 | V | 1442.8 | DMFA | 1304.4 |
| Fe | 3321.5 | W | 2063.5 | DMAA | 1451.5 |
| Ni | 383.8 | Ce | 1011.2 | THF | 1203.1 |

TABLE 9-continued

| M1 | M1ave | M2 | M2ave | Cosolvent | CS ave |
|---|---|---|---|---|---|
| Pb | 387.7 | La | 914.1 | DiGly | 1219.5 |
| Re | 423.7 | Sn | 945.3 | DEAA | 1198.4 |

In the second iteration of the process, experimental formulations consist of six chemical species shown in TABLE 10. Process parameters are shown in TABLE 11.

TABLE 10

| | Formulation Type Parameter Variation | Formulation Amount Parameter Variation |
|---|---|---|
| Precious metal catalyst | Held Constant | Held Constant |
| Metal Catalyst 1 (M1) | Fe or Cu (as their acetylacetonates) | 5,20 (as molar ratios to precious metal catalyst) |
| Metal Catalyst 2 (M2) | V or W (as their acetylacetonates) | 5,20 (as molar ratios to precious metal catalyst) |
| Cosolvent (CS) | Dimethylformamide (DMFA) or Dimethylacetamide (DMAA) | Varied independently in amount. Possible values were 500, 4000 (as molar ratios to precious metal catalyst) |
| Hydroxyaromatic compound | Held constant | Sufficient added to achieve constant sample volume |

TABLE 11

| Process Parameter | Process Parameter Variation |
|---|---|
| Pressure | 1000 psi, 1500 psi (8% Oxygen in Carbon Monoxide) |
| Temperature | 100 C, 120 C |
| Reaction Time | 1 hour, 2 hours |

Size of an initial chemical space defined by the parameters of TABLE 10 and TABLE 11 is calculated as 512 possibilities. The 512 possibilities are organized into an experiment of the type known as a "full factorial design" with pressure, temperature, and reaction time parameters "blocked." A full factorial design is an experiment with >1 adjustable control parameters (factors) each of which can take on >1 value (levels). In a full factorial design experiment, an observation is taken at each of all possible combinations of levels that can be formed from the different factors. A full factorial design is capable of estimating all possible effects of the factors, including main effects and all interactions. The design is necessary where the intention of an experiment is to determine if there are unusual interactions, particularly between process and formulation variables. Where factors are "blocked," factors that are relatively difficult to quickly vary are grouped together. A full factorial design for the chemical space of this Example is shown in TABLE 12.

TABLE 12

| Block | M1 | M1 amt. | M2 | M2 amt. | CS | CS amt. | Pressure | Temperature | Time | TON |
|---|---|---|---|---|---|---|---|---|---|---|
| 2 | Cu | 5 | W | 5 | DMFA | 500 | 1000 | 100 | 2 | 4806.417 |
| 2 | Fe | 20 | W | 5 | DMFA | 500 | 1000 | 100 | 2 | 3321.028 |
| 2 | Cu | 20 | W | 5 | DMFA | 500 | 1000 | 100 | 2 | 5529.844 |
| 2 | Fe | 5 | V | 20 | DMFA | 500 | 1000 | 100 | 2 | 3145.139 |
| 2 | Cu | 5 | V | 20 | DMFA | 500 | 1000 | 100 | 2 | 5495.893 |
| 2 | Fe | 20 | V | 20 | DMFA | 500 | 1000 | 100 | 2 | 2599.752 |
| 2 | Cu | 20 | V | 20 | DMFA | 500 | 1000 | 100 | 2 | 4521.231 |
| 2 | Fe | 5 | W | 20 | DMFA | 500 | 1000 | 100 | 2 | 3139.919 |

TABLE 12-continued

| Block | M1 | M1 amt. | M2 | M2 amt. | CS | CS amt. | Pressure | Temperature | Time | TON |
|---|---|---|---|---|---|---|---|---|---|---|
| 2 | Cu | 5 | W | 20 | DMFA | 500 | 1000 | 100 | 2 | 5106.096 |
| 2 | Fe | 20 | W | 20 | DMFA | 500 | 1000 | 100 | 2 | 3252.493 |
| 2 | Cu | 20 | W | 20 | DMFA | 500 | 1000 | 100 | 2 | 5025.739 |
| 2 | Fe | 5 | V | 5 | DMAA | 500 | 1000 | 100 | 2 | 2801.16 |
| 2 | Cu | 5 | V | 5 | DMAA | 500 | 1000 | 100 | 2 | 5625.641 |
| 2 | Fe | 20 | V | 5 | DMAA | 500 | 1000 | 100 | 2 | 2995.132 |
| 2 | Cu | 20 | V | 5 | DMAA | 500 | 1000 | 100 | 2 | 4854.658 |
| 2 | Fe | 5 | W | 5 | DMAA | 500 | 1000 | 100 | 2 | 2743.656 |
| 2 | Cu | 5 | W | 5 | DMAA | 500 | 1000 | 100 | 2 | 4617.833 |
| 2 | Fe | 20 | W | 5 | DMAA | 500 | 1000 | 100 | 2 | 3023.491 |
| 2 | Cu | 20 | W | 5 | DMAA | 500 | 1000 | 100 | 2 | 5087.621 |
| 2 | Fe | 5 | V | 20 | DMAA | 500 | 1000 | 100 | 2 | 3259.962 |
| 2 | Cu | 5 | V | 20 | DMAA | 500 | 1000 | 100 | 2 | 5375.063 |
| 2 | Fe | 20 | V | 20 | DMAA | 500 | 1000 | 100 | 2 | 2816.106 |
| 2 | Cu | 20 | V | 20 | DMAA | 500 | 1000 | 100 | 2 | 4596.62 |
| 2 | Fe | 5 | W | 20 | DMAA | 500 | 1000 | 100 | 2 | 3301.399 |
| 2 | Cu | 5 | W | 20 | DMAA | 500 | 1000 | 100 | 2 | 5095.495 |
| 2 | Fe | 20 | W | 20 | DMAA | 500 | 1000 | 100 | 2 | 3062.839 |
| 2 | Cu | 20 | W | 20 | DMAA | 500 | 1000 | 100 | 2 | 4980.406 |
| 2 | Fe | 5 | V | 5 | DMFA | 4000 | 1000 | 100 | 2 | 5301.676 |
| 2 | Cu | 5 | V | 5 | DMFA | 4000 | 1000 | 100 | 2 | 2992.894 |
| 2 | Fe | 20 | V | 5 | DMFA | 4000 | 1000 | 100 | 2 | 5226.527 |
| 2 | Cu | 20 | V | 5 | DMFA | 4000 | 1000 | 100 | 2 | 3229.047 |
| 2 | Fe | 5 | W | 5 | DMFA | 4000 | 1000 | 100 | 2 | 4741.478 |
| 2 | Cu | 5 | W | 5 | DMFA | 4000 | 1000 | 100 | 2 | 3150.125 |
| 2 | Fe | 20 | W | 5 | DMFA | 4000 | 1000 | 100 | 2 | 4602.754 |
| 2 | Cu | 20 | W | 5 | DMFA | 4000 | 1000 | 100 | 2 | 2719.743 |
| 1 | Fe | 20 | V | 5 | DMFA | 4000 | 1000 | 100 | 1 | 4345.231 |
| 1 | Cu | 20 | V | 5 | DMFA | 4000 | 1000 | 100 | 1 | 2177.339 |
| 1 | Fe | 5 | W | 5 | DMFA | 4000 | 1000 | 100 | 1 | 4439.784 |
| 1 | Cu | 5 | W | 5 | DMFA | 4000 | 1000 | 100 | 1 | 1915.281 |
| 1 | Fe | 20 | W | 5 | DMFA | 4000 | 1000 | 100 | 1 | 3416.777 |
| 1 | Cu | 20 | W | 5 | DMFA | 4000 | 1000 | 100 | 1 | 1906.395 |
| 1 | Fe | 5 | V | 20 | DMFA | 4000 | 1000 | 100 | 1 | 3955.658 |
| 1 | Cu | 5 | V | 20 | DMFA | 4000 | 1000 | 100 | 1 | 2068.799 |
| 1 | Fe | 20 | V | 20 | DMFA | 4000 | 1000 | 100 | 1 | 3757.099 |
| 1 | Cu | 20 | V | 20 | DMFA | 4000 | 1000 | 100 | 1 | 2195.421 |
| 1 | Fe | 5 | W | 20 | DMFA | 4000 | 1000 | 100 | 1 | 4265.04 |
| 1 | Cu | 5 | W | 20 | DMFA | 4000 | 1000 | 100 | 1 | 2622.194 |
| 1 | Fe | 20 | W | 20 | DMFA | 4000 | 1000 | 100 | 1 | 4080.135 |
| 1 | Cu | 20 | W | 20 | DMFA | 4000 | 1000 | 100 | 1 | 2165.103 |
| 1 | Fe | 5 | V | 5 | DMAA | 4000 | 1000 | 100 | 1 | 3917.162 |
| 1 | Cu | 5 | V | 5 | DMAA | 4000 | 1000 | 100 | 1 | 2401.285 |
| 1 | Fe | 20 | V | 5 | DMAA | 4000 | 1000 | 100 | 1 | 3756.023 |
| 1 | Cu | 20 | V | 5 | DMAA | 4000 | 1000 | 100 | 1 | 1860.372 |
| 1 | Fe | 5 | W | 5 | DMAA | 4000 | 1000 | 100 | 1 | 3812.629 |
| 1 | Cu | 5 | W | 5 | DMAA | 4000 | 1000 | 100 | 1 | 1539.843 |
| 1 | Fe | 20 | W | 5 | DMAA | 4000 | 1000 | 100 | 1 | 4062.504 |
| 1 | Cu | 20 | W | 5 | DMAA | 4000 | 1000 | 100 | 1 | 2322.649 |
| 1 | Fe | 5 | V | 20 | DMAA | 4000 | 1000 | 100 | 1 | 4085.449 |
| 1 | Cu | 5 | V | 20 | DMAA | 4000 | 1000 | 100 | 1 | 1662.921 |
| 1 | Fe | 20 | V | 20 | DMAA | 4000 | 1000 | 100 | 1 | 4030.069 |
| 1 | Cu | 20 | V | 20 | DMAA | 4000 | 1000 | 100 | 1 | 2271.779 |
| 1 | Fe | 5 | W | 20 | DMAA | 4000 | 1000 | 100 | 1 | 4267.062 |
| 1 | Cu | 5 | W | 20 | DMAA | 4000 | 1000 | 100 | 1 | 2020.112 |
| 1 | Fe | 20 | W | 20 | DMAA | 4000 | 1000 | 100 | 1 | 4066.339 |
| 1 | Cu | 20 | W | 20 | DMAA | 4000 | 1000 | 100 | 1 | 1900.791 |
| 2 | Fe | 5 | V | 5 | DMFA | 500 | 1000 | 100 | 2 | 3700.711 |
| 2 | Cu | 5 | V | 5 | DMFA | 500 | 1000 | 100 | 2 | 5105.03 |
| 2 | Fe | 20 | V | 5 | DMFA | 500 | 1000 | 100 | 2 | 3043.119 |
| 2 | Cu | 20 | V | 5 | DMFA | 500 | 1000 | 100 | 2 | 4908.279 |
| 2 | Fe | 5 | W | 5 | DMFA | 500 | 1000 | 100 | 2 | 2899.673 |
| 3 | Fe | 20 | W | 20 | DMFA | 4000 | 1000 | 120 | 1 | 1286.159 |
| 3 | Cu | 20 | W | 20 | DMFA | 4000 | 1000 | 120 | 1 | 3052.865 |
| 3 | Fe | 5 | V | 5 | DMAA | 4000 | 1000 | 120 | 1 | 1140.058 |
| 3 | Cu | 5 | V | 5 | DMAA | 4000 | 1000 | 120 | 1 | 2545.555 |
| 3 | Fe | 20 | V | 5 | DMAA | 4000 | 1000 | 120 | 1 | 1075.588 |
| 3 | Cu | 20 | V | 5 | DMAA | 4000 | 1000 | 120 | 1 | 3170.971 |
| 3 | Fe | 5 | W | 5 | DMAA | 4000 | 1000 | 120 | 1 | 1025.795 |
| 3 | Cu | 5 | W | 5 | DMAA | 4000 | 1000 | 120 | 1 | 3205.365 |
| 3 | Fe | 20 | W | 5 | DMAA | 4000 | 1000 | 120 | 1 | 1144.007 |
| 3 | Cu | 20 | W | 5 | DMAA | 4000 | 1000 | 120 | 1 | 3073.614 |
| 3 | Fe | 5 | V | 20 | DMAA | 4000 | 1000 | 120 | 1 | 991.2687 |
| 3 | Cu | 5 | V | 20 | DMAA | 4000 | 1000 | 120 | 1 | 2875.273 |
| 3 | Fe | 20 | V | 20 | DMAA | 4000 | 1000 | 120 | 1 | 987.423 |
| 3 | Cu | 20 | V | 20 | DMAA | 4000 | 1000 | 120 | 1 | 3169.661 |
| 3 | Fe | 5 | W | 20 | DMAA | 4000 | 1000 | 120 | 1 | 1393.893 |

TABLE 12-continued

| Block | M1 | M1 amt. | M2 | M2 amt. | CS | CS amt. | Pressure | Temperature | Time | TON |
|---|---|---|---|---|---|---|---|---|---|---|
| 3 | Cu | 5 | W | 20 | DMAA | 4000 | 1000 | 120 | 1 | 3361.081 |
| 3 | Fe | 20 | W | 20 | DMAA | 4000 | 1000 | 120 | 1 | 1464.002 |
| 3 | Cu | 20 | W | 20 | DMAA | 4000 | 1000 | 120 | 1 | 3221.897 |
| 4 | Fe | 5 | V | 5 | DMFA | 500 | 1000 | 120 | 2 | 3562.027 |
| 4 | Cu | 5 | V | 5 | DMFA | 500 | 1000 | 120 | 2 | 1169.025 |
| 4 | Fe | 20 | V | 5 | DMFA | 500 | 1000 | 120 | 2 | 3065.418 |
| 4 | Cu | 20 | V | 5 | DMFA | 500 | 1000 | 120 | 2 | 1179.965 |
| 4 | Fe | 5 | W | 5 | DMFA | 500 | 1000 | 120 | 2 | 3167.984 |
| 4 | Cu | 5 | W | 5 | DMFA | 500 | 1000 | 120 | 2 | 1297.288 |
| 4 | Fe | 20 | W | 5 | DMFA | 500 | 1000 | 120 | 2 | 2967.498 |
| 4 | Cu | 20 | W | 5 | DMFA | 500 | 1000 | 120 | 2 | 502.1629 |
| 4 | Fe | 5 | V | 20 | DMFA | 500 | 1000 | 120 | 2 | 3156.959 |
| 4 | Cu | 5 | V | 20 | DMFA | 500 | 1000 | 120 | 2 | 1254.915 |
| 4 | Fe | 20 | V | 20 | DMFA | 500 | 1000 | 120 | 2 | 3403.2 |
| 4 | Cu | 20 | V | 20 | DMFA | 500 | 1000 | 120 | 2 | 1311.478 |
| 4 | Fe | 5 | W | 20 | DMFA | 500 | 1000 | 120 | 2 | 3215.089 |
| 4 | Cu | 5 | W | 20 | DMFA | 500 | 1000 | 120 | 2 | 801.7368 |
| 4 | Fe | 20 | W | 20 | DMFA | 500 | 1000 | 120 | 2 | 2463.873 |
| 4 | Cu | 20 | W | 20 | DMFA | 500 | 1000 | 120 | 2 | 1286.28 |
| 4 | Fe | 5 | V | 5 | DMAA | 500 | 1000 | 120 | 2 | 3225.547 |
| 2 | Fe | 5 | V | 20 | DMFA | 4000 | 1000 | 100 | 2 | 5004.734 |
| 2 | Cu | 5 | V | 20 | DMFA | 4000 | 1000 | 100 | 2 | 3115.677 |
| 2 | Fe | 20 | V | 20 | DMFA | 4000 | 1000 | 100 | 2 | 4969.642 |
| 2 | Cu | 20 | V | 20 | DMFA | 4000 | 1000 | 100 | 2 | 2806.752 |
| 2 | Fe | 5 | W | 20 | DMFA | 4000 | 1000 | 100 | 2 | 4879.942 |
| 2 | Cu | 5 | W | 20 | DMFA | 4000 | 1000 | 100 | 2 | 2891.03 |
| 2 | Fe | 20 | W | 20 | DMFA | 4000 | 1000 | 100 | 2 | 4912.866 |
| 2 | Cu | 20 | W | 20 | DMFA | 4000 | 1000 | 100 | 2 | 3036.185 |
| 2 | Fe | 5 | V | 5 | DMAA | 4000 | 1000 | 100 | 2 | 4437.605 |
| 2 | Cu | 5 | V | 5 | DMAA | 4000 | 1000 | 100 | 2 | 2880.5 |
| 2 | Fe | 20 | V | 5 | DMAA | 4000 | 1000 | 100 | 2 | 5043.313 |
| 2 | Cu | 20 | V | 5 | DMAA | 4000 | 1000 | 100 | 2 | 2875.502 |
| 2 | Fe | 5 | W | 5 | DMAA | 4000 | 1000 | 100 | 2 | 4705.449 |
| 2 | Cu | 5 | W | 5 | DMAA | 4000 | 1000 | 100 | 2 | 3012.273 |
| 2 | Fe | 20 | W | 5 | DMAA | 4000 | 1000 | 100 | 2 | 5032.286 |
| 2 | Cu | 20 | W | 5 | DMAA | 4000 | 1000 | 100 | 2 | 2658.891 |
| 2 | Fe | 5 | V | 20 | DMAA | 4000 | 1000 | 100 | 2 | 4690.863 |
| 2 | Cu | 5 | V | 20 | DMAA | 4000 | 1000 | 100 | 2 | 2695.653 |
| 2 | Fe | 20 | V | 20 | DMAA | 4000 | 1000 | 100 | 2 | 5029.318 |
| 2 | Cu | 20 | V | 20 | DMAA | 4000 | 1000 | 100 | 2 | 2964.375 |
| 2 | Fe | 5 | W | 20 | DMAA | 4000 | 1000 | 100 | 2 | 4540.673 |
| 2 | Cu | 5 | W | 20 | DMAA | 4000 | 1000 | 100 | 2 | 2848.039 |
| 2 | Fe | 20 | W | 20 | DMAA | 4000 | 1000 | 100 | 2 | 4994.425 |
| 2 | Cu | 20 | W | 20 | DMAA | 4000 | 1000 | 100 | 2 | 3097.556 |
| 3 | Fe | 5 | V | 5 | DMFA | 500 | 1000 | 120 | 1 | 3096.222 |
| 3 | Cu | 5 | V | 5 | DMFA | 500 | 1000 | 120 | 1 | 1130.108 |
| 3 | Fe | 20 | V | 5 | DMFA | 500 | 1000 | 120 | 1 | 3223.721 |
| 3 | Cu | 20 | V | 5 | DMFA | 500 | 1000 | 120 | 1 | 1391.525 |
| 3 | Fe | 5 | W | 5 | DMFA | 500 | 1000 | 120 | 1 | 3367.514 |
| 3 | Cu | 5 | W | 5 | DMFA | 500 | 1000 | 120 | 1 | 735.8303 |
| 3 | Fe | 20 | W | 5 | DMFA | 500 | 1000 | 120 | 1 | 3063.38 |
| 3 | Cu | 20 | W | 5 | DMFA | 500 | 1000 | 120 | 1 | 1264.4 |
| 3 | Fe | 5 | V | 20 | DMFA | 500 | 1000 | 120 | 1 | 3286.707 |
| 3 | Cu | 5 | V | 20 | DMFA | 500 | 1000 | 120 | 1 | 1162.79 |
| 3 | Fe | 20 | V | 20 | DMFA | 500 | 1000 | 120 | 1 | 3153.402 |
| 5 | Cu | 20 | W | 5 | DMAA | 500 | 1200 | 100 | 1 | 4260.867 |
| 5 | Fe | 5 | V | 20 | DMAA | 500 | 1200 | 100 | 1 | 1845.083 |
| 5 | Cu | 5 | V | 20 | DMAA | 500 | 1200 | 100 | 1 | 4220.054 |
| 5 | Fe | 20 | V | 20 | DMAA | 500 | 1200 | 100 | 1 | 2422.747 |
| 5 | Cu | 20 | V | 20 | DMAA | 500 | 1200 | 100 | 1 | 4208.349 |
| 5 | Fe | 5 | W | 20 | DMAA | 500 | 1200 | 100 | 1 | 2461.61 |
| 5 | Cu | 5 | W | 20 | DMAA | 500 | 1200 | 100 | 1 | 4414.644 |
| 5 | Fe | 20 | W | 20 | DMAA | 500 | 1200 | 100 | 1 | 2320.681 |
| 5 | Cu | 20 | W | 20 | DMAA | 500 | 1200 | 100 | 1 | 4131.439 |
| 5 | Fe | 5 | V | 5 | DMFA | 4000 | 1200 | 100 | 1 | 3764.029 |
| 5 | Cu | 5 | V | 5 | DMFA | 4000 | 1200 | 100 | 1 | 2456.474 |
| 5 | Fe | 20 | V | 5 | DMFA | 4000 | 1200 | 100 | 1 | 4196.127 |
| 5 | Cu | 20 | V | 5 | DMFA | 4000 | 1200 | 100 | 1 | 2489.818 |
| 5 | Fe | 5 | W | 5 | DMFA | 4000 | 1200 | 100 | 1 | 4326.255 |
| 5 | Cu | 5 | W | 5 | DMFA | 4000 | 1200 | 100 | 1 | 1798.646 |
| 5 | Fe | 20 | W | 5 | DMFA | 4000 | 1200 | 100 | 1 | 4552.989 |
| 5 | Cu | 20 | W | 5 | DMFA | 4000 | 1200 | 100 | 1 | 2438.734 |
| 5 | Fe | 5 | V | 20 | DMFA | 4000 | 1200 | 100 | 1 | 4899.729 |
| 5 | Cu | 5 | V | 20 | DMFA | 4000 | 1200 | 100 | 1 | 1766.201 |
| 5 | Fe | 20 | V | 20 | DMFA | 4000 | 1200 | 100 | 1 | 3853.274 |
| 5 | Cu | 20 | V | 20 | DMFA | 4000 | 1200 | 100 | 1 | 2205.384 |
| 5 | Fe | 5 | W | 20 | DMFA | 4000 | 1200 | 100 | 1 | 4483.398 |

TABLE 12-continued

| Block | M1 | M1 amt. | M2 | M2 amt. | CS | CS amt. | Pressure | Temperature | Time | TON |
|---|---|---|---|---|---|---|---|---|---|---|
| 5 | Cu | 5 | W | 20 | DMFA | 4000 | 1200 | 100 | 1 | 2193.717 |
| 5 | Fe | 20 | W | 20 | DMFA | 4000 | 1200 | 100 | 1 | 3915.764 |
| 5 | Cu | 20 | W | 20 | DMFA | 4000 | 1200 | 100 | 1 | 2130.307 |
| 5 | Fe | 5 | V | 5 | DMAA | 4000 | 1200 | 100 | 1 | 4268.58 |
| 5 | Cu | 5 | V | 5 | DMAA | 4000 | 1200 | 100 | 1 | 2449.769 |
| 5 | Fe | 20 | V | 5 | DMAA | 4000 | 1200 | 100 | 1 | 4051.658 |
| 5 | Cu | 20 | V | 5 | DMAA | 4000 | 1200 | 100 | 1 | 2319.5 |
| 5 | Fe | 5 | W | 5 | DMAA | 4000 | 1200 | 100 | 1 | 4182.63 |
| 5 | Cu | 5 | W | 5 | DMAA | 4000 | 1200 | 100 | 1 | 1913.637 |
| 5 | Fe | 20 | W | 5 | DMAA | 4000 | 1200 | 100 | 1 | 4171.779 |
| 5 | Cu | 20 | W | 5 | DMAA | 4000 | 1200 | 100 | 1 | 1788.613 |
| 6 | Fe | 5 | V | 20 | DMAA | 4000 | 1200 | 100 | 1 | 4304.112 |
| 6 | Cu | 5 | V | 20 | DMAA | 4000 | 1200 | 100 | 1 | 2340.053 |
| 4 | Cu | 5 | V | 5 | DMAA | 500 | 1000 | 120 | 2 | 1027.837 |
| 4 | Fe | 20 | V | 5 | DMAA | 500 | 1000 | 120 | 2 | 3455.892 |
| 4 | Cu | 20 | V | 5 | DMAA | 500 | 1000 | 120 | 2 | 1167.907 |
| 4 | Fe | 5 | W | 5 | DMAA | 500 | 1000 | 120 | 2 | 3040.422 |
| 4 | Cu | 5 | W | 5 | DMAA | 500 | 1000 | 120 | 2 | 1625.673 |
| 4 | Fe | 20 | W | 5 | DMAA | 500 | 1000 | 120 | 2 | 2649.228 |
| 4 | Cu | 20 | W | 5 | DMAA | 500 | 1000 | 120 | 2 | 1075.155 |
| 4 | Fe | 5 | V | 20 | DMAA | 500 | 1000 | 120 | 2 | 3454.219 |
| 4 | Cu | 5 | V | 20 | DMAA | 500 | 1000 | 120 | 2 | 1726.461 |
| 4 | Fe | 20 | V | 20 | DMAA | 500 | 1000 | 120 | 2 | 3407.73 |
| 4 | Cu | 20 | V | 20 | DMAA | 500 | 1000 | 120 | 2 | 1391.012 |
| 4 | Fe | 5 | W | 20 | DMAA | 500 | 1000 | 120 | 2 | 3375.964 |
| 4 | Cu | 5 | W | 20 | DMAA | 500 | 1000 | 120 | 2 | 1620.468 |
| 4 | Fe | 20 | W | 20 | DMAA | 500 | 1000 | 120 | 2 | 3347.955 |
| 4 | Cu | 20 | W | 20 | DMAA | 500 | 1000 | 120 | 2 | 1227.624 |
| 4 | Fe | 5 | V | 5 | DMFA | 4000 | 1000 | 120 | 2 | 1285.104 |
| 4 | Cu | 5 | V | 5 | DMFA | 4000 | 1000 | 120 | 2 | 3131.439 |
| 4 | Fe | 20 | V | 5 | DMFA | 4000 | 1000 | 120 | 2 | 1191.938 |
| 4 | Cu | 20 | V | 5 | DMFA | 4000 | 1000 | 120 | 2 | 3019.846 |
| 4 | Fe | 5 | W | 5 | DMFA | 4000 | 1000 | 120 | 2 | 1598.604 |
| 4 | Cu | 5 | W | 5 | DMFA | 4000 | 1000 | 120 | 2 | 3058.827 |
| 4 | Fe | 20 | W | 5 | DMFA | 4000 | 1000 | 120 | 2 | 1111.198 |
| 4 | Cu | 20 | W | 5 | DMFA | 4000 | 1000 | 120 | 2 | 3429.221 |
| 4 | Fe | 5 | V | 20 | DMFA | 4000 | 1000 | 120 | 2 | 1584.459 |
| 4 | Cu | 5 | V | 20 | DMFA | 4000 | 1000 | 120 | 2 | 3624.455 |
| 4 | Fe | 20 | V | 20 | DMFA | 4000 | 1000 | 120 | 2 | 1352.145 |
| 4 | Cu | 20 | V | 20 | DMFA | 4000 | 1000 | 120 | 2 | 3281.384 |
| 4 | Fe | 5 | W | 20 | DMFA | 4000 | 1000 | 120 | 2 | 1323.115 |
| 4 | Cu | 5 | W | 20 | DMFA | 4000 | 1000 | 120 | 2 | 3189.967 |
| 4 | Fe | 20 | W | 20 | DMFA | 4000 | 1000 | 120 | 2 | 1523.089 |
| 4 | Cu | 20 | W | 20 | DMFA | 4000 | 1000 | 120 | 2 | 3211.642 |
| 4 | Fe | 5 | V | 5 | DMAA | 4000 | 1000 | 120 | 2 | 1342.161 |
| 4 | Cu | 5 | V | 5 | DMAA | 4000 | 1000 | 120 | 2 | 3207.565 |
| 4 | Fe | 20 | V | 5 | DMAA | 4000 | 1000 | 120 | 2 | 1494.474 |
| 4 | Cu | 20 | V | 5 | DMAA | 4000 | 1000 | 120 | 2 | 3022.931 |
| 7 | Cu | 20 | V | 5 | DMFA | 4000 | 1200 | 120 | 1 | 3393.315 |
| 7 | Fe | 5 | W | 5 | DMFA | 4000 | 1200 | 120 | 1 | 1403.261 |
| 7 | Cu | 5 | W | 5 | DMFA | 4000 | 1200 | 120 | 1 | 3555.009 |
| 7 | Fe | 20 | W | 5 | DMFA | 4000 | 1200 | 120 | 1 | 1308.279 |
| 7 | Cu | 20 | W | 5 | DMFA | 4000 | 1200 | 120 | 1 | 3512.98 |
| 7 | Fe | 5 | V | 20 | DMFA | 4000 | 1200 | 120 | 1 | 1284.812 |
| 7 | Cu | 5 | V | 20 | DMFA | 4000 | 1200 | 120 | 1 | 3435.316 |
| 7 | Fe | 20 | V | 20 | DMFA | 4000 | 1200 | 120 | 1 | 1694.665 |
| 7 | Cu | 20 | V | 20 | DMFA | 4000 | 1200 | 120 | 1 | 3496.463 |
| 7 | Fe | 5 | W | 20 | DMFA | 4000 | 1200 | 120 | 1 | 1143.947 |
| 7 | Cu | 5 | W | 20 | DMFA | 4000 | 1200 | 120 | 1 | 3456.876 |
| 7 | Fe | 20 | W | 20 | DMFA | 4000 | 1200 | 120 | 1 | 1617.505 |
| 7 | Cu | 20 | W | 20 | DMFA | 4000 | 1200 | 120 | 1 | 3879.49 |
| 7 | Fe | 5 | V | 5 | DMAA | 4000 | 1200 | 120 | 1 | 1273.745 |
| 7 | Cu | 5 | V | 5 | DMAA | 4000 | 1200 | 120 | 1 | 3382.074 |
| 7 | Fe | 20 | V | 5 | DMAA | 4000 | 1200 | 120 | 1 | 881.0287 |
| 7 | Cu | 20 | V | 5 | DMAA | 4000 | 1200 | 120 | 1 | 3104.413 |
| 7 | Fe | 5 | W | 5 | DMAA | 4000 | 1200 | 120 | 1 | 1395.572 |
| 7 | Cu | 5 | W | 5 | DMAA | 4000 | 1200 | 120 | 1 | 3141.805 |
| 7 | Fe | 20 | W | 5 | DMAA | 4000 | 1200 | 120 | 1 | 1774.357 |
| 7 | Cu | 20 | W | 5 | DMAA | 4000 | 1200 | 120 | 1 | 3413.901 |
| 8 | Fe | 5 | V | 20 | DMAA | 4000 | 1200 | 120 | 1 | 1649.139 |
| 8 | Cu | 5 | V | 20 | DMAA | 4000 | 1200 | 120 | 1 | 3368.794 |
| 8 | Fe | 20 | V | 20 | DMAA | 4000 | 1200 | 120 | 1 | 1824.133 |
| 8 | Cu | 20 | V | 20 | DMAA | 4000 | 1200 | 120 | 1 | 3660.883 |
| 8 | Fe | 5 | W | 20 | DMAA | 4000 | 1200 | 120 | 1 | 1179.379 |
| 8 | Cu | 5 | W | 20 | DMAA | 4000 | 1200 | 120 | 1 | 3628.204 |
| 8 | Fe | 20 | W | 20 | DMAA | 4000 | 1200 | 120 | 1 | 1293.674 |
| 8 | Cu | 20 | W | 20 | DMAA | 4000 | 1200 | 120 | 1 | 3019.058 |

TABLE 12-continued

| Block | M1 | M1 amt. | M2 | M2 amt. | CS | CS amt. | Pressure | Temperature | Time | TON |
|---|---|---|---|---|---|---|---|---|---|---|
| 8 | Fe | 5 | V | 5 | DMFA | 500 | 1200 | 120 | 2 | 2990.086 |
| 8 | Cu | 5 | V | 5 | DMFA | 500 | 1200 | 120 | 2 | 1029.93 |
| 8 | Fe | 20 | V | 5 | DMFA | 500 | 1200 | 120 | 2 | 3062.541 |
| 8 | Cu | 20 | V | 5 | DMFA | 500 | 1200 | 120 | 2 | 1242.527 |
| 8 | Fe | 5 | W | 5 | DMFA | 500 | 1200 | 120 | 2 | 3147.093 |
| 8 | Cu | 5 | W | 5 | DMFA | 500 | 1200 | 120 | 2 | 1316.01 |
| 6 | Fe | 20 | V | 20 | DMAA | 4000 | 1200 | 100 | 1 | 3973.3 |
| 6 | Cu | 20 | V | 20 | DMAA | 4000 | 1200 | 100 | 1 | 2242.964 |
| 6 | Fe | 5 | W | 20 | DMAA | 4000 | 1200 | 100 | 1 | 4220.131 |
| 6 | Cu | 5 | W | 20 | DMAA | 4000 | 1200 | 100 | 1 | 2029.409 |
| 6 | Fe | 20 | W | 20 | DMAA | 4000 | 1200 | 100 | 1 | 4474.279 |
| 6 | Cu | 20 | W | 20 | DMAA | 4000 | 1200 | 100 | 1 | 2185.812 |
| 6 | Fe | 5 | V | 5 | DMFA | 500 | 1200 | 100 | 2 | 3200.736 |
| 6 | Cu | 5 | V | 5 | DMFA | 500 | 1200 | 100 | 2 | 5251.12 |
| 6 | Fe | 20 | V | 5 | DMFA | 500 | 1200 | 100 | 2 | 2941.772 |
| 6 | Cu | 20 | V | 5 | DMFA | 500 | 1200 | 100 | 2 | 5348.456 |
| 6 | Fe | 5 | W | 5 | DMFA | 500 | 1200 | 100 | 2 | 3216.89 |
| 6 | Cu | 5 | W | 5 | DMFA | 500 | 1200 | 100 | 2 | 5601.562 |
| 6 | Fe | 20 | W | 5 | DMFA | 500 | 1200 | 100 | 2 | 3213.059 |
| 6 | Cu | 20 | W | 5 | DMFA | 500 | 1200 | 100 | 2 | 5455.892 |
| 6 | Fe | 5 | V | 20 | DMFA | 500 | 1200 | 100 | 2 | 3248.214 |
| 6 | Cu | 5 | V | 20 | DMFA | 500 | 1200 | 100 | 2 | 4972.636 |
| 6 | Fe | 20 | V | 20 | DMFA | 500 | 1200 | 100 | 2 | 3355.542 |
| 6 | Cu | 20 | V | 20 | DMFA | 500 | 1200 | 100 | 2 | 5019.747 |
| 6 | Fe | 5 | W | 20 | DMFA | 500 | 1200 | 100 | 2 | 3747.147 |
| 6 | Cu | 5 | W | 20 | DMFA | 500 | 1200 | 100 | 2 | 5053.546 |
| 6 | Fe | 20 | W | 20 | DMFA | 500 | 1200 | 100 | 2 | 3082.532 |
| 6 | Cu | 20 | W | 20 | DMFA | 500 | 1200 | 100 | 2 | 5055.11 |
| 6 | Fe | 5 | V | 5 | DMAA | 500 | 1200 | 100 | 2 | 2903.681 |
| 6 | Cu | 5 | V | 5 | DMAA | 500 | 1200 | 100 | 2 | 4726.624 |
| 6 | Fe | 20 | V | 5 | DMAA | 500 | 1200 | 100 | 2 | 3378.448 |
| 6 | Cu | 20 | V | 5 | DMAA | 500 | 1200 | 100 | 2 | 5179.236 |
| 6 | Fe | 5 | W | 5 | DMAA | 500 | 1200 | 100 | 2 | 3013.919 |
| 6 | Cu | 5 | W | 5 | DMAA | 500 | 1200 | 100 | 2 | 4803.361 |
| 6 | Fe | 20 | W | 5 | DMAA | 500 | 1200 | 100 | 2 | 3213.767 |
| 6 | Cu | 20 | W | 5 | DMAA | 500 | 1200 | 100 | 2 | 5545.379 |
| 6 | Fe | 5 | V | 20 | DMAA | 500 | 1200 | 100 | 2 | 3585.461 |
| 6 | Cu | 5 | V | 20 | DMAA | 500 | 1200 | 100 | 2 | 4672.836 |
| 6 | Fe | 20 | V | 20 | DMAA | 500 | 1200 | 100 | 2 | 3238.526 |
| 6 | Cu | 20 | V | 20 | DMAA | 500 | 1200 | 100 | 2 | 5161.146 |
| 6 | Fe | 5 | W | 20 | DMAA | 500 | 1200 | 100 | 2 | 3014.8 |
| 8 | Fe | 20 | W | 5 | DMFA | 500 | 1200 | 120 | 2 | 3127.044 |
| 8 | Cu | 20 | W | 5 | DMFA | 500 | 1200 | 120 | 2 | 1729.955 |
| 8 | Fe | 5 | V | 20 | DMFA | 500 | 1200 | 120 | 2 | 3923.339 |
| 8 | Cu | 5 | V | 20 | DMFA | 500 | 1200 | 120 | 2 | 1251.202 |
| 8 | Fe | 20 | V | 20 | DMFA | 500 | 1200 | 120 | 2 | 3291.114 |
| S | Cu | 20 | V | 20 | DMFA | 500 | 1200 | 120 | 2 | 1309.178 |
| 8 | Fe | 5 | W | 20 | DMFA | 500 | 1200 | 120 | 2 | 3166.405 |
| 8 | Cu | 5 | W | 20 | DMFA | 500 | 1200 | 120 | 2 | 1079.929 |
| 8 | Fe | 20 | W | 20 | DMFA | 500 | 1200 | 120 | 2 | 3399.78 |
| 8 | Cu | 20 | W | 20 | DMFA | 500 | 1200 | 120 | 2 | 1317.061 |
| 8 | Fe | 5 | V | 5 | DMAA | 500 | 1200 | 120 | 2 | 3249.165 |
| 8 | Cu | 5 | V | 5 | DMAA | 500 | 1200 | 120 | 2 | 1310.566 |
| 8 | Fe | 20 | V | 5 | DMAA | 500 | 1200 | 120 | 2 | 3181.768 |
| 8 | Cu | 20 | V | 5 | DMAA | 500 | 1200 | 120 | 2 | 1384.317 |
| 8 | Fe | 5 | W | 5 | DMAA | 500 | 1200 | 120 | 2 | 3483.545 |
| 8 | Cu | 5 | W | 5 | DMAA | 500 | 1200 | 120 | 2 | 1483.464 |
| 8 | Fe | 20 | W | 5 | DMAA | 500 | 1200 | 120 | 2 | 3243.016 |
| 8 | Cu | 20 | W | 5 | DMAA | 500 | 1200 | 120 | 2 | 1659.831 |
| 8 | Fe | 5 | V | 20 | DMAA | 500 | 1200 | 120 | 2 | 3832.087 |
| 8 | Cu | 5 | V | 20 | DMAA | 500 | 1200 | 120 | 2 | 1434.119 |
| 8 | Fe | 20 | V | 20 | DMAA | 500 | 1200 | 120 | 2 | 3898.378 |
| 8 | Cu | 20 | V | 20 | DMAA | 500 | 1200 | 120 | 2 | 1514.125 |
| 8 | Fe | 5 | W | 20 | DMAA | 500 | 1200 | 120 | 2 | 3320.126 |
| 8 | Cu | 5 | W | 20 | DMAA | 500 | 1200 | 120 | 2 | 1269.161 |
| 8 | Fe | 20 | W | 20 | DMAA | 500 | 1200 | 120 | 2 | 3552.422 |
| 8 | Cu | 20 | W | 20 | DMAA | 500 | 1200 | 120 | 2 | 1408.177 |
| 8 | Fe | 5 | V | 5 | DMFA | 4000 | 1200 | 120 | 2 | 1330.367 |
| 8 | Cu | 5 | V | 5 | DMFA | 4000 | 1200 | 120 | 2 | 3233.872 |
| 8 | Fe | 20 | V | 5 | DMFA | 4000 | 1200 | 120 | 2 | 1119.671 |
| 8 | Cu | 20 | V | 5 | DMFA | 4000 | 1200 | 120 | 2 | 3565.294 |
| 8 | Fe | 5 | W | 5 | DMFA | 4000 | 1200 | 120 | 2 | 1540.59 |
| 8 | Cu | 5 | W | 5 | DMFA | 4000 | 1200 | 120 | 2 | 3197.359 |
| 8 | Fe | 20 | W | 5 | DMFA | 4000 | 1200 | 120 | 2 | 1421.148 |
| 8 | Cu | 20 | W | 5 | DMFA | 4000 | 1200 | 120 | 2 | 3467.429 |
| 8 | Fe | 5 | V | 20 | DMFA | 4000 | 1200 | 120 | 2 | 1265.396 |

In this iteration, each of the metal acetylacetonates, the DMAA, and the DMFA is made up as a stock solution in phenol. An appropriate quantity of each stock solution is then combined using a Hamilton MicroLab 4000 laboratory robot into a single vial for mixing. For example, the stock solutions to produce rows 1, 65, 129, 193, 257, 321, 385, and 449 or TABLE 12, are 0.01 molar Pd(acetylacetonate), 0.01 molar each of Fe(acetylacetonate) and V(acetylacetonate) and 5 molar DMFA. Ten ml of each stock solution is produced by manual weighing and mixing. Aliquots of the stock solutions are measured as follows in TABLE 13. The mixture is stirred using a miniature magnetic stirrer.

TABLE 13

| | |
|---|---|
| 0.01 molar Pd(acetylacetonate) | 25 microliters |
| 0.01 molar Fe(acetylacetonate) | 125 microliters |
| 0.01 molar V(acetylacetonate) | 125 microliters |
| 5 molar DMFA | 25 microliters |
| Pure Phenol | 700 microliters |

In the second iteration, pressure chamber reactor 54 is heated and pressurized. to the conditions shown as Block 1 in TABLE 7. The procedure described as iteration 1 is repeated in the system described with reference to FIG. 3 and FIG. 4 with the species of TABLE 10. This process is repeated until all the block conditions have been run.

The performance of each vial is given in the column "TON" of TABLE 13. These results are then analyzed using a "General Linear Model" (GLM) routine in Minitab software. A GLM routine performs analysis of variance (ANOVA) on any specified mathematical model potentially describing a relationship between control factors and response. The routine determines which terms of the model actually have a statistically significant influence on response. The GLM routine is set to calculate an Analysis of Variance (ANOVA) for all main effects, 2-way interactions, and 3-way interactions in data. In a factorial design, an effect of a factor is the average change in response when the value of that factor is changed from its low level to its high level. The effect is a main effect when it is calculated without including the influence of other factors. A 2-way interaction mathematically describes change in the effect of one factor when a second factor is changed from its low level to its high level. A 3-way interaction mathematically describes change in the effect of one factor when two other factors simultaneously are changed from respective low levels to respective high levels.

The ANOVA in this Example is given in TABLE 14.

TABLE 14

| Source | DF | Seq SS | Adj SS | Adj MS | F Ratio | P | Significant at P < 0.01 |
|---|---|---|---|---|---|---|---|
| M1 amt | 1 | 16412 | 16412 | 16412 | 0.201 | 0.654 | |
| M2 amt | 1 | 77926 | 77926 | 77926 | 0.954 | 0.329 | |
| CS amt | 1 | 33586 | 33586 | 33586 | 0.411 | 0.522 | |
| Pressure | 1 | 4616039 | 4616039 | 4616039 | 56.526 | 0.000 | YES |
| Temperature | 1 | 216802139 | 216802139 | 216802139 | 2654.854 | 0.000 | YES |
| Time | 1 | 31205785 | 31205785 | 31205785 | 382.131 | 0.000 | YES |
| M1 | 1 | 22404811 | 22404811 | 22404811 | 274.358 | 0.000 | YES |
| M2 | 1 | 182205 | 182205 | 182205 | 2.231 | 0.136 | |
| CS | 1 | 3702 | 3702 | 3702 | 0.045 | 0.832 | |
| M1 amt*M2 amt | 1 | 27036 | 27036 | 27036 | 0.331 | 0.565 | |
| M1 amt*CS amt | 1 | 58292 | 58292 | 58292 | 0.714 | 0.399 | |
| M1 amt*Pressure | 1 | 61467 | 61467 | 61467 | 0.753 | 0.386 | |
| M1 amt*Temperature | 1 | 26926 | 26926 | 26926 | 0.330 | 0.566 | |
| M1 amt*Time | 1 | 110415 | 110415 | 110415 | 1.352 | 0.246 | |
| M1 amt*M1 | 1 | 34335 | 34335 | 34335 | 0.420 | 0.517 | |
| M1 amt*M2 | 1 | 232680 | 232680 | 232680 | 2.849 | 0.092 | |
| M1 amt*CS | 1 | 260446 | 260446 | 260446 | 3.189 | 0.075 | |
| M2 amt*CS amt | 1 | 79627 | 79627 | 79627 | 0.975 | 0.324 | |
| M2 amt*Pressure | 1 | 341447 | 341447 | 341447 | 4.181 | 0.042 | |
| M2 amt*Temperature | 1 | 477 | 477 | 477 | 0.006 | 0.939 | |
| M2 amt*Time | 1 | 125869 | 125869 | 125869 | 1.541 | 0.215 | |
| M2 amt*M1 | 1 | 14190 | 14190 | 14190 | 0.174 | 0.677 | |
| M2 amt*M2 | 1 | 81553 | 81553 | 81553 | 0.999 | 0.318 | |
| M2 amt*CS | 1 | 8125 | 8125 | 8125 | 0.099 | 0.753 | |
| CS amt*Pressure | 1 | 33749 | 33749 | 33749 | 0.413 | 0.521 | |
| CS amt*Temperature | 1 | 295416 | 295416 | 295416 | 3.618 | 0.058 | |
| CS amt*Time | 1 | 7438 | 7438 | 7438 | 0.091 | 0.763 | |
| CS amt*M1 | 1 | 132568 | 132568 | 132568 | 1.623 | 0.203 | |
| CS amt*M2 | 1 | 37280 | 37280 | 37280 | 0.457 | 0.500 | |
| CS amt*CS | 1 | 23702 | 23702 | 23702 | 0.290 | 0.590 | |
| Pressure*Temperature | 1 | 40272 | 40272 | 40272 | 0.493 | 0.483 | |
| Pressure*Time | 1 | 38 | 38 | 38 | 0.000 | 0.983 | |
| Pressure*M1 | 1 | 253770 | 253770 | 253770 | 3.108 | 0.079 | |
| Pressure*M2 | 1 | 260899 | 260899 | 260899 | 3.195 | 0.075 | |
| Pressure*CS | 1 | 11954 | 11954 | 11954 | 0.146 | 0.702 | |
| Temperature*Time | 1 | 33291520 | 33291520 | 33291520 | 407.672 | 0.000 | YES |
| Temperature*M1 | 1 | 43430 | 43430 | 43430 | 0.532 | 0.466 | |
| Temperature*M2 | 1 | 94767 | 94767 | 94767 | 1.160 | 0.282 | |
| Temperature*CS | 1 | 90412 | 90412 | 90412 | 1.107 | 0.293 | |
| Time*M1 | 1 | 1491 | 1491 | 1491 | 0.018 | 0.893 | |
| Time*M2 | 1 | 93605 | 93605 | 93605 | 1.146 | 0.285 | |
| Time*CS | 1 | 76043 | 76043 | 76043 | 0.931 | 0.335 | |
| M1*M2 | 1 | 77799 | 77799 | 77799 | 0.953 | 0.330 | |

TABLE 14-continued

| Source | DF | Seq SS | Adj SS | Adj MS | F Ratio | Significant P at P < 0.01 |
|---|---|---|---|---|---|---|
| M1*CS | 1 | 169760 | 169760 | 169760 | 2.079 | 0.150 |
| M2*CS | 1 | 407136 | 407136 | 407136 | 4.986 | 0.026 |
| M1 amt*M2 amt*CS amt | 1 | 361079 | 361079 | 361079 | 4.422 | 0.036 |
| M1 amt*M2 amt*Pressure | 1 | 21432 | 21432 | 21432 | 0.262 | 0.609 |
| M1 amt*M2 amt*Temperature | 1 | 271 | 271 | 271 | 0.003 | 0.954 |
| M1 amt*M2 amt*Time | 1 | 13991 | 13991 | 13991 | 0.171 | 0.679 |
| M1 amt*M2 amt*M1 | 1 | 281433 | 281433 | 281433 | 3.446 | 0.064 |
| M1 amt*M2 amt*M2 | 1 | 1 | 1 | 1 | 0.000 | 0.997 |
| M1 amt*M2 amt*CS | 1 | 116073 | 116073 | 116073 | 1.421 | 0.234 |
| M1 amt*CS amt*Pressure | 1 | 114627 | 114627 | 114627 | 1.404 | 0.237 |
| M1 amt*CS amt*Temperature | 1 | 466 | 466 | 466 | 0.006 | 0.940 |
| M1 amt*CS amt*Time | 1 | 69157 | 69157 | 69157 | 0.847 | 0.358 |
| M1 amt*CS amt*M1 | 1 | 164860 | 164860 | 164860 | 2.019 | 0.156 |
| M1 amt*CS amt*M2 | 1 | 14698 | 14698 | 14698 | 0.180 | 0.672 |
| M1 amt*CS amt*CS | 1 | 334131 | 334131 | 334131 | 4.092 | 0.044 |
| M1 amt*Pressure*Temperature | 1 | 235 | 235 | 235 | 0.003 | 0.957 |
| M1 amt*Pressure*Time | 1 | 167809 | 167809 | 167809 | 2.055 | 0.153 |
| M1 amt*Pressure*M1 | 1 | 8172 | 8172 | 8172 | 0.100 | 0.752 |
| M1 amt*Pressure*M2 | 1 | 4377 | 4377 | 4377 | 0.054 | 0.817 |
| M1 amt*Pressure*CS | 1 | 6356 | 6356 | 6356 | 0.078 | 0.780 |
| M1 amt*Temperature*Time | 1 | 67161 | 67161 | 67161 | 0.822 | 0.365 |
| M1 amt*Temperature*M1 | 1 | 194664 | 194664 | 194664 | 2.384 | 0.123 |
| M1 amt*Temperature*M2 | 1 | 569 | 569 | 569 | 0.007 | 0.934 |
| M1 amt*Temperature*CS | 1 | 11 | 11 | 11 | 0.000 | 0.991 |
| M1 amt*Time*M1 | 1 | 6489 | 6489 | 6489 | 0.079 | 0.778 |
| M1 amt*Time*M2 | 1 | 30862 | 30862 | 30862 | 0.378 | 0.539 |
| M1 amt*Time*CS | 1 | 163612 | 163612 | 163612 | 2.004 | 0.158 |
| M1 amt*M1*M2 | 1 | 77397 | 77397 | 77397 | 0.948 | 0.331 |
| M1 amt*M1*CS | 1 | 11421 | 11421 | 11421 | 0.140 | 0.709 |
| M2 amt*M2*CS | 1 | 59409 | 59409 | 59409 | 0.727 | 0.394 |
| M2 amt*CS amt*Pressure | 1 | 6344 | 6344 | 6344 | 0.078 | 0.781 |
| M2 amt*CS amt*Temperature | 1 | 0 | 0 | 0 | 0.000 | 1.000 |
| M2 amt*CS amt*Time | 1 | 70019 | 70019 | 70019 | 0.857 | 0.355 |
| M2 amt*CS amt*M1 | 1 | 89887 | 89887 | 89887 | 1.101 | 0.295 |
| M2 amt*CS amt*M2 | 1 | 120523 | 120523 | 120523 | 1.476 | 0.225 |
| M2 amt*CS amt*CS | 1 | 8479 | 8479 | 8479 | 0.104 | 0.747 |
| M2 amt*Pressure*Temperature | 1 | 190090 | 190090 | 190090 | 2.328 | 0.128 |
| M2 amt*Pressure*Time | 1 | 14716 | 14716 | 14716 | 0.180 | 0.671 |
| M2 amt*Pressure*M1 | 1 | 7373 | 7373 | 7373 | 0.090 | 0.764 |
| M2 amt*Pressure*M2 | 1 | 16357 | 16357 | 16357 | 0.200 | 0.655 |
| M2 amt*Pressure*CS | 1 | 35027 | 35027 | 35027 | 0.429 | 0.513 |
| M2 amt*Temperature*Time | 1 | 26831 | 26831 | 26831 | 0.329 | 0.567 |
| M2 amt*Temperature*M1 | 1 | 626 | 626 | 626 | 0.008 | 0.930 |
| M2 amt*Temperature*M2 | 1 | 94448 | 94448 | 94448 | 1.157 | 0.283 |
| M2 amt*Temperature*CS | 1 | 1212 | 1212 | 1212 | 0.015 | 0.903 |
| M2 amt*Time*M1 | 1 | 77055 | 77055 | 77055 | 0.944 | 0.332 |
| M2 amt*Time*M2 | 1 | 6233 | 6233 | 6233 | 0.076 | 0.782 |
| M2 amt*Time*CS | 1 | 337817 | 337817 | 337817 | 4.137 | 0.043 |
| M2 amt*M1*M2 | 1 | 38653 | 38653 | 38653 | 0.473 | 0.492 |
| M2 amt*M1*CS | 1 | 23751 | 23751 | 23751 | 0.291 | 0.590 |
| M2 amt*M2*CS | 1 | 3270 | 3270 | 3270 | 0.040 | 0.842 |
| CS amt*Pressure*Temperature | 1 | 84561 | 84561 | 84561 | 1.035 | 0.310 |
| CS amt*Pressure*Time | 1 | 212868 | 212868 | 212868 | 2.607 | 0.107 |
| CS amt*Pressure*M1 | 1 | 34495 | 34495 | 34495 | 0.422 | 0.516 |
| CS amt*Pressure*M2 | 1 | 20299 | 20299 | 20299 | 0.249 | 0.618 |
| CS amt*Pressure*CS | 1 | 12034 | 12034 | 12034 | 0.147 | 0.701 |
| CS amt*Temperature*Time | 1 | 174636 | 174636 | 174636 | 2.139 | 0.144 |
| CS amt*Temperature*M1 | 1 | 535239896 | 535239896 | 535239896 | 6554.288 | 0.000 YES |
| CS amt*Temperature*M2 | 1 | 4708 | 4708 | 4708 | 0.058 | 0.810 |
| CS amt*Temperature*CS | 1 | 331 | 331 | 331 | 0.004 | 0.949 |
| CS amt*Time*M1 | 1 | 112874 | 112874 | 112874 | 1.382 | 0.240 |
| CS amt*Time*M2 | 1 | 1469 | 1469 | 1469 | 0.018 | 0.893 |
| CS amt*Time*CS | 1 | 804 | 804 | 804 | 0.010 | 0.921 |
| CS amt*M1*M2 | 1 | 75785 | 75785 | 75785 | 0.928 | 0.336 |
| CS amt*M1*CS | 1 | 22036 | 22036 | 22036 | 0.270 | 0.604 |
| CS amt*M2*CS | 1 | 34743 | 34743 | 34743 | 0.425 | 0.515 |
| Pressure*Temperature*Time | 1 | 950930 | 950930 | 950930 | 11.645 | 0.001 YES |

TABLE 14-continued

| Source | DF | Seq SS | Adj SS | Adj MS | F Ratio | Significant P at P < 0.01 |
|---|---|---|---|---|---|---|
| Pressure*Temperature*M1 | 1 | 18226 | 18226 | 18226 | 0.223 | 0.637 |
| Pressure*Temperature*M2 | 1 | 11544 | 11544 | 11544 | 0.141 | 0.707 |
| Pressure*Temperature*CS | 1 | 67428 | 67428 | 67428 | 0.826 | 0.364 |
| Pressure*Time*M1 | 1 | 310071 | 310071 | 310071 | 3.797 | 0.052 |
| Pressure*Time*M2 | 1 | 10784 | 10784 | 10784 | 0.132 | 0.717 |
| Pressure*Time*CS | 1 | 2008 | 2008 | 2008 | 0.025 | 0.875 |
| Pressure*M1*M2 | 1 | 12343 | 12343 | 12343 | 0.151 | 0.698 |
| Pressure*M1*CS | 1 | 14220 | 14220 | 14220 | 0.174 | 0.677 |
| Pressure*M2*CS | 1 | 67936 | 67936 | 67936 | 0.832 | 0.362 |
| Temperature*Time*M1 | 1 | 221695 | 221695 | 221695 | 2.715 | 0.100 |
| Temperature*Time*M2 | 1 | 38 | 38 | 38 | 0.000 | 0.983 |
| Temperature*Time*CS | 1 | 10 | 10 | 10 | 0.000 | 0.991 |
| Temperature*M1*M2 | 1 | 24040 | 24040 | 24040 | 0.294 | 0.588 |
| Temperature*M1*CS | 1 | 257092 | 257092 | 257092 | 3.148 | 0.077 |
| Temperature*M2*CS | 1 | 848 | 848 | 848 | 0.010 | 0.919 |
| Time*M1*M2 | 1 | 53303 | 53303 | 53303 | 0.653 | 0.420 |
| Time*M1*CS | 1 | 44080 | 44080 | 44080 | 0.540 | 0.463 |
| Time*M2*CS | 1 | 7295 | 7295 | 7295 | 0.089 | 0.765 |
| M1*M2*CS | 1 | 319669 | 319669 | 319669 | 3.915 | 0.049 |
| Error | 382 | 31195094 | 31195094 | 81662.55 | | |
| Total | 511 | 885328201 | | | | |

Figure 5:
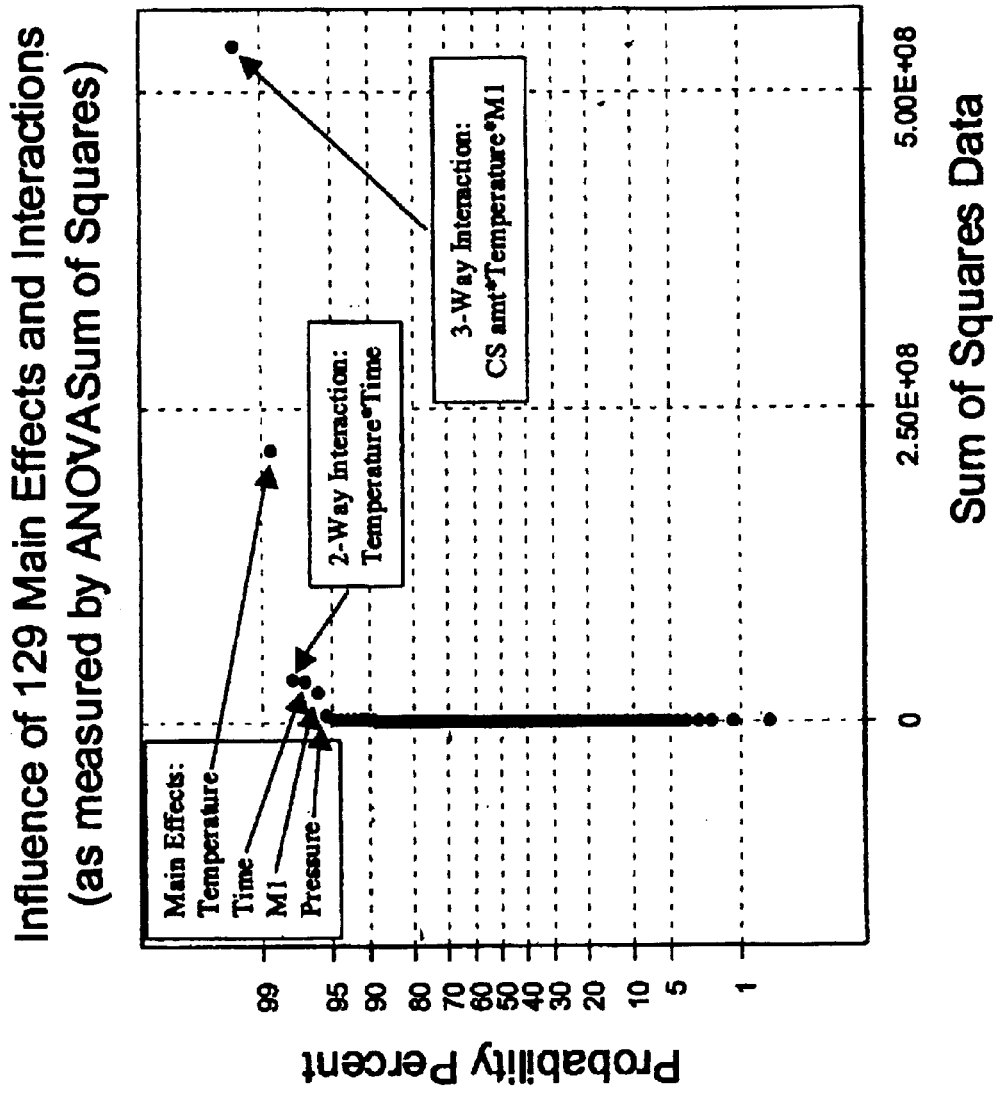
FIG. 5 is a graph showing influence of effects and interactions utilizing an embodiment of the present invention.

The column "Significant at P<0.01" of TABLE 14 defines the factors and interactions in the model, which have a statistically significant effect on the response with a probability of incorrect decision of less than 1%. The column shows that only 5 of the 129 possible main effects, 2-way interactions, and 3-way interactions have a significant effect on the TON. It is noted that a 3-way interaction (CS amt*Temperature*M1) has the largest influence on the TON (FIG. 5).

This Example shows that the disclosed method can perform large numbers of experiments and can sort out variables in a combinatorial experiment to detect key process interactions. From this interaction a favorable condition for obtaining high (>5500) TON is determined as shown in TABLE 15.

TABLE 15

| Factor | Identity | Amount |
|---|---|---|
| M1 | Cu | Any |
| M2 | Any | Any |
| CS | Any | 500 |
| Pressure | | Any |
| Temperature | | 100C |
| Time | | 2 hr |

The interaction identifies a unique condition in which two formulation variables (M1=Cu and CS amount=500) generate a very high level of TON only when the temperature is at 100° C.

It will be understood that each of the elements described above, or two or more together, may also find utility in applications differing from the types described herein. While the invention has been illustrated and described as embodied in a sequential high-throughput screening method and system, it is not intended to be limited to the details shown, since various modifications and substitutions can be made without departing in any way from the spirit of the present invention. For example, robotic equipment can be used to prepare samples and various types of parallel analytical screening methods can be incorporated. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A synthesis system, comprising a vessel for combinatorial chemical process having:
   a charge port comprising an air lock capable of sequentially receiving a plurality of discrete combinations of reactants;
   a vertically longitudinal reaction chamber in communication with said charge port, said reaction chamber being capable of receiving and enclosing the plurality of discrete combinations of reactants disposed linearly within said chamber; and
   a discharge port comprising an air lock, distinct from said charge port, in communication with said vertically longitudinal reaction chamber to sequentially discharge reaction products of said combinations from said reaction chamber;
   wherein said vertically longitudinal reaction chamber is adapted to receive each of said combinations of reactants in a vial by sequential gravity loading from the charge port.

2. The system of claim 1, wherein said charge port and said discharge port each comprises an air lock controlled by a ball valve.

3. The system of claim 1, further comprising a detector proximate to said discharge port to detect said sequentially discharged reaction product from said reaction chamber.

4. The system of claim 1, further comprising a controller in communication with said reaction vessel to control varying reaction parameters within said chamber.

5. The system of claim 1, further comprising a controller in communication with said reaction vessel to control a sequence of charging said combinations of reactants to said chamber or a sequence of discharging said products from said chamber.

6. The system of claim 1, further comprising a detector in communication with said discharge port to detect said sequentially discharged reaction products and a processor in communication with said controller and said detector to correlate reaction or reactant variables with a corresponding reaction product.

a detector proximate to said discharge port to detect said sequentially discharged reaction product from said reaction chamber; and a controller in communication with said reaction vessel to control varying reaction parameters within said chamber.

* * * * *